US007732148B2

(12) United States Patent
Cahill et al.

(10) Patent No.: US 7,732,148 B2
(45) Date of Patent: Jun. 8, 2010

(54) ANNEXIN A3 FOR PROSTATE CANCER DIAGNOSIS

(75) Inventors: Michael Cahill, Loerzweiler (DE); André Schrattenholz, Mainz (DE)

(73) Assignee: ProteoSys AG (DE)

( * ) Notice: Subject to any disclaimer, the term of this patent is extended or adjusted under 35 U.S.C. 154(b) by 0 days.

(21) Appl. No.: 11/920,822

(22) PCT Filed: May 22, 2006

(86) PCT No.: PCT/EP2006/004818
§ 371 (c)(1),
(2), (4) Date: Nov. 20, 2007

(87) PCT Pub. No.: WO2006/125580
PCT Pub. Date: Nov. 30, 2006

(65) Prior Publication Data
US 2008/0200385 A1 Aug. 21, 2008

(30) Foreign Application Priority Data
May 21, 2005 (EP) .................................. 05011042
Nov. 30, 2005 (EP) .................................. 05026092

(51) Int. Cl.
*G01N 33/53* (2006.01)
*G01N 33/567* (2006.01)
*G01N 33/574* (2006.01)
*C07K 14/00* (2006.01)

(52) U.S. Cl. ...................... 435/7.1; 435/7.21; 435/7.23; 530/350

(58) Field of Classification Search ....................... None
See application file for complete search history.

(56) References Cited

U.S. PATENT DOCUMENTS

| 2002/0110832 | A1* | 8/2002 | Pyle et al. ..................... 435/7.1 |
| 2002/0168696 | A1 | 11/2002 | Hanash et al. |
| 2003/0108963 | A1* | 6/2003 | Schlegel et al. ............ 435/7.23 |
| 2003/0152923 | A1 | 8/2003 | Yakhini et al. |
| 2003/0165954 | A1 | 9/2003 | Katagiri et al. |
| 2003/0175736 | A1 | 9/2003 | Chinnaiyan et al. |
| 2003/0232399 | A1 | 12/2003 | Robertson et al. |
| 2004/0033502 | A1 | 2/2004 | Williams et al. |
| 2004/0096916 | A1 | 5/2004 | Kellner et al. |
| 2004/0241653 | A1* | 12/2004 | Feinstein et al. ............... 435/6 |

FOREIGN PATENT DOCUMENTS

| WO | WO 2004/079368 A2 | 9/2004 |
| WO | WO 2005/078124 A2 | 8/2005 |

OTHER PUBLICATIONS

Stites et al (Medical Immunology, 9th Ed, Appleton and Lange, Stamford, 1997, p. 250-251).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850).*
Kaiser (Science, 2006, 313: 1370).*
Jiang et al (JBC, 2003, 278(7) 4763-4769).*
Matsushita et al (FEBS Letters, 1999, vol. 443, pp. 348-352).*
Singh et al (Glycobiology, 2001, vol. 11, pp. 587-592).*
Le Cabec et al. (Biochemical J. 1994 303:481-487).*
Markku H. Vaarala et al., "Differentially Expressed Genes in Two LNCaP Prostate Cancer Cell Lines Reflecting Changes during Prostate Cancer Progression," Laboratory Investigation, vol. 80, No. 8, Aug. 2000, pp. 1259-1268.
Ayodele A. Alaiya et al., "Protein expression profiling in human lung, breast, bladder, renal, colorectal and ovarian cancers," Journal of Chromatography B: Biomedical Sciences & Applications, vol. 787, No. 1, Apr. 5, 2003, pp. 207-222.
Seung-won Lee et al., "Revealing urologic diseases by proteomic techniques," Journal of Chromatography B: Biomedical Sciences & Applications, vol. 815, No. 1-2, Feb. 5, 2005, pp. 203-213.
Saverio Cinieri et al., "Innovation in care and research: Meeting highlights from the Seventh Milan Breast Cancer Conference (Milan, Jun. 15-17, 2005)," The Breast, vol. 15, No. 2, Apr. 2006, pp. 232-245.
Carter et al., "Improved Biomarkers for Prostate Cancer: A Definite Need," Journal of the National Cancer Institute, Jun. 2, 2004, vol. 96, No. 11, pp. 813-815.
Antenor et al., "Relationship between Initial Prostate Specific Antigen Level and Subsequent Prostate Cancer Detection in a Longitudinal Screening Study," The Journal of Urology, Jul. 2004, vol. 172, pp. 90-93.
Lilja, Hans, "Biology of Prostate-Specific Antigen," Urology 62 (Supplement 5A), Nov. 2003, pp. 27-33.
Watson et al., "Future Opportunities for the Diagnosis and Treatment of Prostate Cancer," Prostate Cancer Prostatic Diseases, 2004, vol. 7, pp. S8-S13.
Demarzo et al., "Pathological and Molecular Aspects of Prostate Cancer," The Lancet, Mar. 15, 2003, vol. 361, pp. 955-964.
Kumar-Sinha et al., "Molecular Markers to Identify Patients at Risk for Recurrence after Primary Treatment for Prostate Cancer," Urology 62 (Supplement 6B), Dec. 29, 2003, pp. 19-35.
Moul et al., "Molecular Markers in Prostate Cancer: The Role in Preoperative Staging," Clinical Prostate Cancer, Jun. 2002, pp. 42-50.
Ahram et al., "Proteomic Analysis of Human Prostate Cancer," Molecular Carcinogenesis, 2002, vol. 33, pp. 9-15.
Petricoin et al., "Proteomic Approaches in Cancer Risk and Response Assessment," Trends Molecular Medicine, Feb. 2004, vol. 10, No. 2, pp. 59-64.
Diamandis, E. P., "Mass Spectrometry as a Diagnostic and a Cancer Biomarker Discovery Tool: Opportunities and Potential Limitations," Molecular & Cellular Proteomics, 2004, vol. 3, pp. 367-378.
Jacobs et al., "Progress and Challenges in Screening for Early Detection of Ovarian Cancer," Molecular & Cellular Proteomics, 2004, vol. 3, pp. 355-366.

(Continued)

*Primary Examiner*—Karen A Canella
*Assistant Examiner*—Peter J Reddig
(74) *Attorney, Agent, or Firm*—DLA Piper (LLP) US

(57) ABSTRACT

A method treats urogenital and/or intestinal tract cancer and includes administering a therapeutically effective amount of at least one annexion protein, annexin of A3, to a mammal.

8 Claims, 9 Drawing Sheets

OTHER PUBLICATIONS

Lapointe et al., "Gene Expression Profiling Identifies Clinically Relevant Subtypes of Prostate Cancer," PNAS, Jan. 20, 2004, vol. 101, No. 3, pp. 811-816.

Rossi et al., "Fatty Acid Synthase Expression Defines Distinct Molecular Signatures in Prostate Cancer," Molecular Cancer Research, Aug. 2003, vol. 1, pp. 707-715.

Parnes et al., "Prostate Cancer Chemoprevention Agent Development: The National Cancer Institute, Division of Cancer Prevention Portfolio," The Journal of Urology, Feb. 2004, vol. 171, pp. S68-S75.

Eastham, J. A., "Multimodal Treatment Strategies Combining Neoadjuvant Hormonal Therapy and/or Chemotherapy with Radical Prostatectomy in High-Risk Localised Prostate Cancer," Expert Opinion Investigating Drugs, 2004, vol. 13, pp. 39-46.

Nebert et al., "Pharmacogenomics and 'Individualized Drug Therapy': High Expectations and Disappointing Achievements," Am. J. Pharmacogenomics, 2003, vol. 3, pp. 361-370.

Gerke et al., "Annexins: From Structure to Function," Physiol. Rev., Apr. 2002. vol. 82, pp. 331-371.

Alaiya et al, "Identification of Proteins in Human Prostate Tumor Material by Two-Dimensional Gel Electrophoresis and Mass Spectrometry," CMLS Cellular and Molecular Life Sciences, 2001, vol. 58, pp. 307-311.

Niimi et al., "Expression of Annexin A3 in Primary Cultured Parenchymal Rat Hepatocytes and Inhibition of DNA Synthesis by Suppression of Annexin A3 Expression Using RNA Interference," Biol. Pharm. Bull., 2005, vol. 28, No. 3, pp. 424-428.

Niimi et al., "Specific Expression of Annexin III in Rat-Small-Hepatocytes," Biochemical and Biophysical Research Communications, 2003, vol. 300, pp. 770-774.

Schartz et al., "From the Antigen-Presenting Cell to the Antigen-Presenting Vesicle: The Exosomes," Current Opinion in Molecular Therapeutics, 2002, vol. 4, No. 4, pp. 372-381.

Pisitkun et al., "Identification and Proteomic Profiling of Exosomes in Human Urine," PNAS, Sep. 7, 2004, vol. 101, No. 36, pp. 13368-13373.

Thery et al., "Proteomic Analysis of Dendritic Cell-Derived Exosomes: A Secreted Subcellular Compartment Distinct from Apoptotic Vesicles," Journal of Immunology, 2001, vol. 166, pp. 7309-7318.

Carlsson et al., "Dominant Prostasome Immunogens for Sperm-Agglutinating Autoantibodies of Infertile Men," Journal of Andrology, Sep./Oct. 2004, vol. 25, No. 5, pp. 699-705.

Oh et al., "Subtractive Proteomic Mapping of the Endothelial Surface in Lung and Solid Tumours for Tissue-Specific Therapy," Nature, Jun. 10, 2004, vol. 429, pp. 629-635.

Reutelingsperger et al., "Annexin V, the Regulator of Phosphatidylserine-Catalyzed Inflammation and Coagulation during Apoptosis," CMLS Cellular and Molecular Life Science, 1997, vol. 53, pp. 527-532.

Perretti et al., "Annexin 1 and the Biology of the Neutrophil," Journal of Leukocyte Biology, Jul. 2004, vol. 75, pp. 25-29.

Maderna et al., "Modulation of Phagocytosis of Apoptotic Neutrophils by Supernatant from Dexamethasone-Treated Macrophages and Annexin-Derived Peptide Ac(2-26)," The Journal of Immunology, 2005, vol. 174, pp. 3727-3733.

Hegmans et al., "Proteomic Analysis of Exosomes Secreted by Human Mesothelioma Cells," American Journal of Pathology, May 2004, vol. 164, No. 5, pp. 1807-1815.

Wang et al., "Annexin-Mediated Ca2+ Influx Regulates Growth Plate Chondrocyte Maturation and Apoptosis," The Journal of Biological Chemistry, Feb. 7, 2003, vol. 278, No. 6, pp. 3762-3769.

Bondanza et al., "Inhibition of Phosphatidylserine Recognition Heightens the Immunogenicity of Irradiated Lymphoma Cells In Vivo," J. Exp. Med., Nov. 1, 2004, vol. 200, No. 9, pp. 1157-1165.

Kamal et al., "An Annexin 1 (ANXA1)-Derived Peptide Inhibits Prototype Antigen-Driven Human T Cell Th1 and Th2 Responses In Vitro," Clinical and Experimental Allergy, 2001, vol. 31, pp. 1116-1125.

Schostak, M. et al., "Annexin A3 in Urine: A Highly Specific Noninvasive Marker for Prostate Cancer Early Detection," *The Journal of Urology*, Jan. 2009, vol. 181, pp. 343-353.

* cited by examiner

ANNEXIN A3 FOR PROSTATE CANCER DIAGNOSIS

RELATED APPLICATIONS

This is a §371 of International Application No. PCT/EP2006/004818, with an international filing date of May 22, 2006 (WO 2006/125580A1, published Nov. 30, 2006), which is based on European Patent Application Nos. 05011042.8, filed May 21, 2005, and 05026092.6, filed Nov. 30, 2005.

TECHNICAL FIELD

This disclosure relates to the treatment and/or diagnosis of cancer, particularly of the urogenital and/or intestinal tract.

BACKGROUND

Cancer is one of the leading causes of human death in the western civilization and often linked with difficulties regarding its diagnosis.

For example, prostate cancer is one of the leading causes of cancer death in men but is a heterogeneous disease that is difficult to diagnose. Predicting the course that an individual tumor will take is almost impossible. The current state of diagnostic prostate cancer markers is essentially based on different isoforms of prostate specific antigen (PSA) and on the whole is not sactisfactory in terms of false negatives and false positives. (1-4). Recently, various alternative molecular markers have been suggested from body fluids or prostate tissue (5-11). At least three different subclasses of prostate cancer have been identified that seem related to tumor grade, incidence of recurrence, and metastases (12). Fatty acid synthase alone defines distinct molecular signatures for prostate cancer (13). Yet, there is urgent remaining need for more elaborate and reliable therapeutic and diagnostic parameters to characterize patients according to their risk of progression to develop novel appropriate multimodal therapy strategies for improved individual cancer control (14-16).

SUMMARY

We provide a method of treating urogenital and/or intestinal tract cancer including administering a therapeutically effective amount of at least one annexin protein, annexin of A3, to a mammal.

We also provide a method of diagnosing urogenital and/or intestinal tract cancer and/or discrimination between cancerous and non-cancerous tissue, including determining abundance of at least one intracellular annexin protein and/or determining abundance of at least one estracellular annexin protein, with urine samples or fractions thereof.

Figure 1:
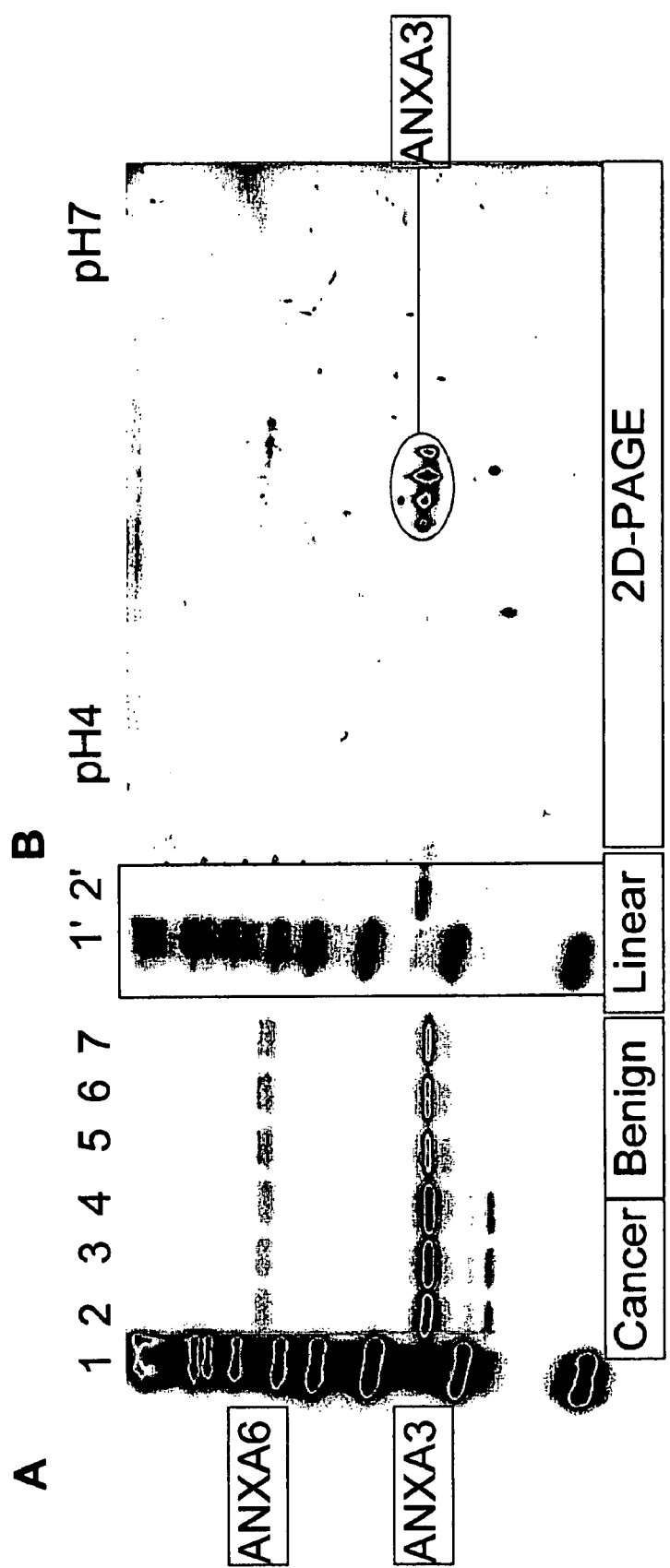
FIG. 1 is a characterization of the anti-annexin A3 rabbit polyclonal antiserum by Western blot. (A) Western blot of 1-D SDS gel. Lane 1: Magic Mark (Invitrogen) molecular weight markers 3 µl per lane, gives masses in kDa of 120, 100, 80, 60, 50, 40, 30, and 20. Replicate lanes contain 15 µg whole tissue protein extract from cancer (Lanes 2-4) and benign (Lanes 5-7) prostate from patient 29. The filter was incubated using anti annexin 3 polyclonal serum (1:20,000). Lanes 1-7 show a false color image of signal from the entire filter. The boxed insert (Lanes 1' and 2') shows the single color depiction of lanes 1 and 2. The positions of annexin A3 and resumed annexin A6 bands are indicated. (B) 2D-PAGE Western blot of protein 100 µg extract from the cancer sample of patient 29 in false color shows the distribution of proteins with cross reactivity to the polyclonal serum. The identity of three strongest (red colored) annexin A3 spots was confirmed by MALDI-TOF PMF (data not shown), the strongest of which corresponds to the protein spot detected in our proteomics analysis.

Area under the ROC curve=0.791
Standard error=0.043
95% Confidence interval=0.703 to 0.863
P (Area=0.5)<0.0001

DETAILED DESCRIPTION

In view thereof, we provide in a first aspect by the use of at least one annexin protein, preferably annexin of A3, for the treatment of cancer, particularly of the urogenital and/or intestinal tract, preferably of prostate cancer.

We also provide for the use of at least one annexin protein, preferably of annexin A3, for the manufacture of a medicament for treatment of cancer, particularly of the urogenital and/or intestinal tract, preferably of prostate cancer. In a preferred aspect, cancer treatment is done by the enhancement of the in vivo abundance of at least one annexin protein, in particular, by the enhancement of the in vivo abundance of at least one extracellular annexin protein.

We further provide methods for diagnosing cancer, particularly of the urogenital and/or intestinal tract, and/or for discrimination between cancerous and non-cancerous tissue comprising the separate steps of:
determining the intracellular abundance of at least one annexin protein and/or
determining the extracellular abundance of at least one annexin protein, in particular using urine samples or fractions thereof.

The method also comprises the separate steps of:
determining the intracellular abundance of at least one annexin protein and
determining the extracellular abundance of at least one annexin protein, in particular using urine samples or fractions thereof.

The method may also comprise the separate steps of:
determining the intracellular abundance of at least one annexin protein and
determining the extracellular abundance of at least one said annexin protein, in particular using urine samples or fractions thereof.

After determination of the intra- and extracellular abundance of at least one annexin protein ratios of the extracellular abundance over the intracellular abundance or the other way around may be determined. Preferably, ratios of the extracellular abundance over the intracellular abundance are determined. The obtained ratios are advantageous diagnostic parameters for cancer and/or for discrimination between cancerous and non-cancerous tissue.

The term "extracellular" is understood as the extracellular space including the outer surface of plasma membranes of cells.

The term "non-cancerous tissue" comprises healthy tissue and pathogenic tissue, in particular benign prostatic hyperplasia, chronic prostatitis, Crohn's disease, colitis ulcerosa, inflammable tissue and fibroses, in particular secondary fibroses.

The term "abundance" is understood as the intracellular and/or extracellular level and concentration respectively of a protein.

The term "annexin protein" and "protein" in general comprise isoforms, mutants, truncated versions and post-translational modified forms thereof. Post-translational modified forms can in particular include proteinaceous forms obtainable by proteolytic processing.

The term "treatment" is equivalent to "therapy," thus comprising the treatment of troubles associated with cancer.

The annexin protein may at least be a member of the group consisting of annexin A1, annexin A2, annexin A3, annexin A4, annexin A5, annexin A6, annexin A7, annexin A8 and annexin A10 and wherein preferably the abundance of the at least one annexin protein is determined together with the abundance of at least a further protein. With respect to the further protein it is referred to the following description.

The abundance of at least one annexin protein may be determined together with the abundance of a small molecule or nucleic acid marker.

Annexins are calcium-binding proteins thought to influence various intra- and extra-cellular functions, including membrane trafficking, lymphocyte migration, cell motility, calcium flux, and signal transduction. They are highly abundant, and the calcium-dependent bulk masking of negatively charged membrane lipids may be important for annexin function (17).

In a previous proteomics study comparing the differential abundance of proteins between benign and tumorous tissue from 31 prostate cancer patiens, we identified annexin A3 as more being variously differentially abundant in tumors and potentially represented a diagnostic marker for various subtypes of prostate cancer. Annexin A3 is a relatively infrequent annexin family member that was upregulated an average of 2.4 fold across all 31 patients (between 1.1 and 5.4 fold with 95% confidence; P=0.045). In a tentative sub-cluster of 22 patients that was suggested by cluster analysis, Annexin A3 was upregulated an average of 4.4 fold (between 2.2 and 9.1 fold with 95% confidence; P=0.0008), suggesting that in certain types of tumor Annexin A3 abundance may be involved in the cancerous phenotype. For further details it is referred to PCT/EP2005/001567, the subject matter of which is incorporated herein in its entirety.

Several annexins are reported to be down-regulated in association with prostate cancer, including annexin A1, annexin A2, annexin A4, annexin A7 and annexin A10 (6). Alaiya et al. (18) also reported "some differential (annexin A3) value between malignant and benign" prostate tissue. Recently, annexin A3 has been shown to be necessary for DNA replication in cultured hepatocytes (19), and seems to be expressed higher in small hepatocytes which have higher growth potential and proliferation rates than parenchymal hepatocytes (20). We thus believe that annexin A3, typically a rare member of this family, may therefore provide a biomarker or target or therapeutic principle for cancer treatment of certain patients.

Annexins are cytoplasmic, but are also found extracellularly, although they lack secretory leader sequences. For instance, Carlsson et al. (24) identified annexin A3 as an antigen for anti-sperm antibodies involved in male infertility. Oh et al. (25) found that annexin A1 was exposed on epithelial surfaces in the vicinity of solid lung tumors, and that administration of a radiolabelled antibody against the protein caused tumor regression in animal experiments. Indeed, annexin A5 translocation to cell surfaces is associated with apoptosis (26), and annexin A1, also known as Lipocortin 1, is released to the extracellular space in large abundances from neutrophils and monocytes/macrophages as an anti-inflammatory agent. In fact, annexin A1 may be the primary mediator of the anti-inflammatory effect of glucocorticoids (27, 28).

There is no mechanism for annexin secretion reported (17) combining secretion, especially the cellular expulsion of annexin A3, the exosome pathway, and altered regulation of immune surveillance of the prostate. Exosomes are membrane vesicles of 30 to 100 nm in diameter, which are produced and secreted in vitro by living cells of diverse origin, and are thought to be involved in the transfer of tumor antigens to antigen presenting cells, as well as in the stimulation of specific immune responses (21). Annexin family members, including annexin A3 and annexin A8, are commonly found in exosomes (21-23).

Hegmann et al. (29) have postulated that exosomes are involved in the release of heat shock proteins to the extracellular environment in the absence of cellular necrosis. The luminal exosome environment could permit the low pH values necessary for the proposed annexin calcium ion channel function in vivo, that has been controversially discussed because of incompatibility with cell viability (17). Indeed, the reported instances of physiological annexin ion channels occur in the matrix vesicles involved in osteoblast bone formation, and in the terminal differentiation and death of chondrocytes (30), which are both circumstances atypical of normal cellular viability. We thus believe that annexin ion channels could be involved in the osmotic rupture of exosome vesicles (either within multivesicular vesicles prior to secretory fusion with the cytoplasmic membrane, or extracellularly) and thereby modulate extracellular milieu of tumors or other tissues, such as bone in the case of osteoporosis.

Bondanza et al. (31) recently reported that irradiated tumor cells are efficiently phagocytized by macrophages, but when cell surface phosphatidylserine is masked by annexin A5, the macrophage pathway is reduced and a strong CD8+ dendritic cell-dependent immune response is elicited. As referred to above, annexin A1 is an anti-inflammatory modulator that reduces neutrophil recruitment, and thereby reduces tissue inflammation. It binds to specific extracellular ALX (lipoxin A) receptors on neutrophils and macrophages, and can thereby modulate macrophage phagocytosis (27, 28). At the site of action within the tissues, annexin A1 and its N-terminal peptide (Ac2-26) promotes phagocytosis of apoptotic neutrophils, thereby reducing the level of inflammation and the immune response through anti-inflammatory cytokines such as TGF(Transforming Growth Factor)-β1 (28), and, accordingly, the antigen-induced T cell proliferation of Th1 (T-helper 1) and Th2 (T-helper 2) T-cells is also inhibted by the peptide Ac2-26 (32). Changes of annexin A3 in tumors may influence immune surveillance of prostate tissue by altering the properties and/or concentration of the extracellular annexin pool, and by thereby modulating the interplay between a macrophage/granulocyte dominated response, and/or a humoral one.

The abundance of at least one annexin protein may be determined together with the abundance of at least another annexin protein, preferably of the group consisting of annexin A1, annexin A2, annexin A3, annexin A4, annexin A5, annexin A6, annexin A7, annexin A8 and annexin A10.

The abundance of at least one annexin protein may also be determined together with the abundance of at least a further protein of the group consisting of serum amyloid P, isopeptidase T, muscle-type fatty acid binding protein, galectin 1, heat shock protein 90, BiP (Human protein: P11021-78 kDa glucose-regulated protein precursor, GRP 78, Immunoglobulin heavy chain binding protein, Endoplasmic reticulum lumenal Ca2+ binding protein grp78), protein disulfide isomerase, epiderrnal-type fatty acid binding protein, enoyl coenzyme A hydratase and nucleophosmin.

Furthermore, the abundance of at least one annexin protein can be determined together with the abundance of at least a further protein of the group consisting of 14-3-3 family, proteasome, particularly prosome and/or macropain, activator subunit 2, cytokeratin family, KNP-I alpha protein (NCBI ACCESSION BAA95554.1 GI:7768772) and KNP-I beta protein (NCBI ACCESSION BAA21139.1 GI:2250701).

In some cases the diagnostic value of conventional tumor markers for diagnosis is limited. For instance, high or extremely low serum prostate antigen (PSA) values provide a reasonable reliable diagnostic index for prostate cancer. However, preoperative PSA values ranging between 2 and 10 ng/ml, especially between 4 and 10 ng/ml, particularly between 2 and 6 ng/ml, are extremely poor regarding diagnostic reliability, in particular with respect to prediction of postoperative cure rates in radical prostatectomies.

Thus, in a particular preferred aspect the abundance of at least one annexin protein is determined together with the abundance of at least one blood or serum marker, in particular of at least one member of the Kallikrein protease family, preferably of prostate specific antigen (PSA). The abundance of various forms of PSA, in particular total PSA (tPSA) abundances, relative or absolute abundances of free PSA (FPSA) and relative or absolute abundances of complexed PSA (cPSA), may be determined together with the abundance of annexin A3. It is further within the scope of this disclosure that other members of the Kallikrein protease family may be used in this respect. The abundances of these proteins to one another may also be used in combination with one or more measured or calculated annexin parameters for diagnostic purposes. The annexin parameters that can be useful are obviously not restricted to those used by way of demonstration in this disclosure.

The abundance of at least one annexin protein may also be determined together with the abundance of at least an epithelial cell marker, particularly prostate specific membrane antigen (PSMA).

According to an especially preferred aspect, annexin A3 and/or annexin A8, preferably annexin A3, are used.

The cancer to be treated and/or diagnosed can be derived from the urogenital and/or intestinal tract. Preferably, cancer is chosen from the group consisting of prostate cancer, kidney cancer, bladder cancer, urethra cancer, ovarian cancer, uterine cancer or colon cancer. Preferably, the cancer to be diagnosed is prostate cancer and/or colon cancer. With respect to prostate cancer, the method preferably allows for discrimination between prostate cancer tissue samples, benign prostatic hyperplasia (BPH) tissue samples, chronic prostatitis tissue samples, fibrosis afflicted tissue samples and healthy tissue samples.

Concerning cancer of the intestinal tract, particularly colon cancer, the method preferably allows for discrimination between cancer tissue sample and samples of tissue which are affected by inflammatory bowel diseases, particularly Crohns's disease and/or colitis ulcerosa.

It is possible to treat and/or to diagnose subgroups of cancers. Furthermore, different cancer stages may be treated and/or diagnosed. It is further possible to monitor the transition of non-cancerous tissue into cancerous tissue.

In a further preferred aspect, excrement samples or fractions thereof, especially of urine, in particular of exprimate urine, are subjected to a separation process prior to determining the abundance of at least one annexin protein to yield cell pellets and supernatants. Preferably, the separation process is done by centrifugation, especially by low speed centrifugation of cells out of a liquid medium (e.g., 200×g for 5 minutes at 4° C.). Any suitable centrifugation protocol, including successive centrifugations under different conditions, or combinations of centrifugations with other methods, may be employed to separate soluble or exosome-bound annexin from intracellular annexin for measurement. Other means of separation of soluble or exosome-bound annexin from intracellular annexin can also be employed, or combinations thereof (e.g., magnetic beads, filtration, chromatography, etc).

The cell pellets may be used for determining the intracellular abundance of at least one annexin protein, preferably of annexin A3.

As already mentioned in the above description, annexins are intricately involved in processes of osteoblastosis and osteolysis. Annexins are implicated in the process of bone mineralization. This is noteworthy because prostate cancer metastases are unusual among cancers in exhibiting a high frequency of osteoblastic bone lesions. Most cancer metastases are characterized by osteoclast osteolytic (bone dissolving) activity, whereas prostate metastases exhibit both osteoclastic and mineral depositing osteoblastic activity.

Physiological mineralization is a highly complex and regulated process. Bone mineralization is initiated by small vesicles, called matrix vesicles, that are released from the plasma membrane of mineralizing skeletal cells. The first mineral phase forms inside the matrix vesicles. Since these are membrane-enclosed, channel proteins are required for the mineral ions to enter. Annexins form channels into the matrix vesicles by which $Ca^{2+}$ enters, leading to the initiation of calcium phosphate mineralization. Once the intravesicular crystals reach a certain size they rupture the membrane. This is in turn related to inflammation, a feature common to cancer and annexin biology, and involves an interplay between bone and the immune system. Therefore, the method can be used to diagnose and/or treat osteoporosis. The method annexin abundances, preferably the abundance of annexin A3 and/or annexin A8, may be determined in body fluids, body secretions, tissue samples, groups of cells or cells, especially by methods known to those skilled in the art to diagnose and/or treat osteoporosis. Such treatment may involve the application of substances that influence the abundance, subcellular/extracellular localisation, post-translational modification or activity of annexin proteins. Activity in this respect especially includes ion-channel activity, which may be appropriately increased or decreased. Substances that may be used for the treatment of osteoporosis explicitly include annexin A3, truncated or mutant versions thereof, or antibodies or other affinity reagents. The substances can further include nucleic acids, or chemically related substances, such as peptide nucleic acids (pNA), which may be also used a small interfering RNAs (siRNAs) as known in the art.

Figure 3:
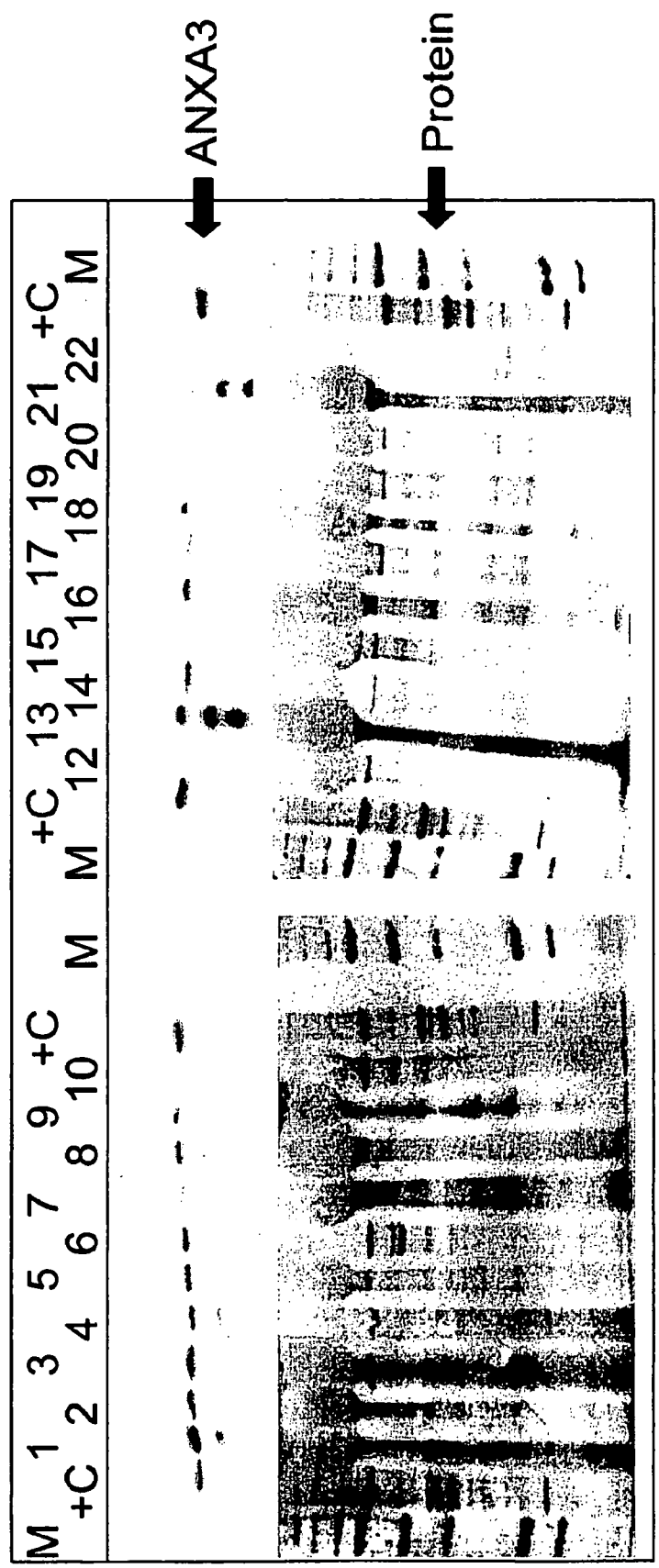
FIG. 3: Western blot quantification of annexin A3 in exprimate pellets of urine obtained after prostatic massage of cancer patients. The top panels show the chemiluminescent annexin A3 signal from blotted proteins. The bottom panels show the loaded protein stained with Ponceau S ('Protein'). Each gel contains a molecular weight ladder (M) as well as duplicates of 7.5 µg of total cell protein lysate from a prostate tumor containing annexin A3 as a positive control (+C).
Figure 4:
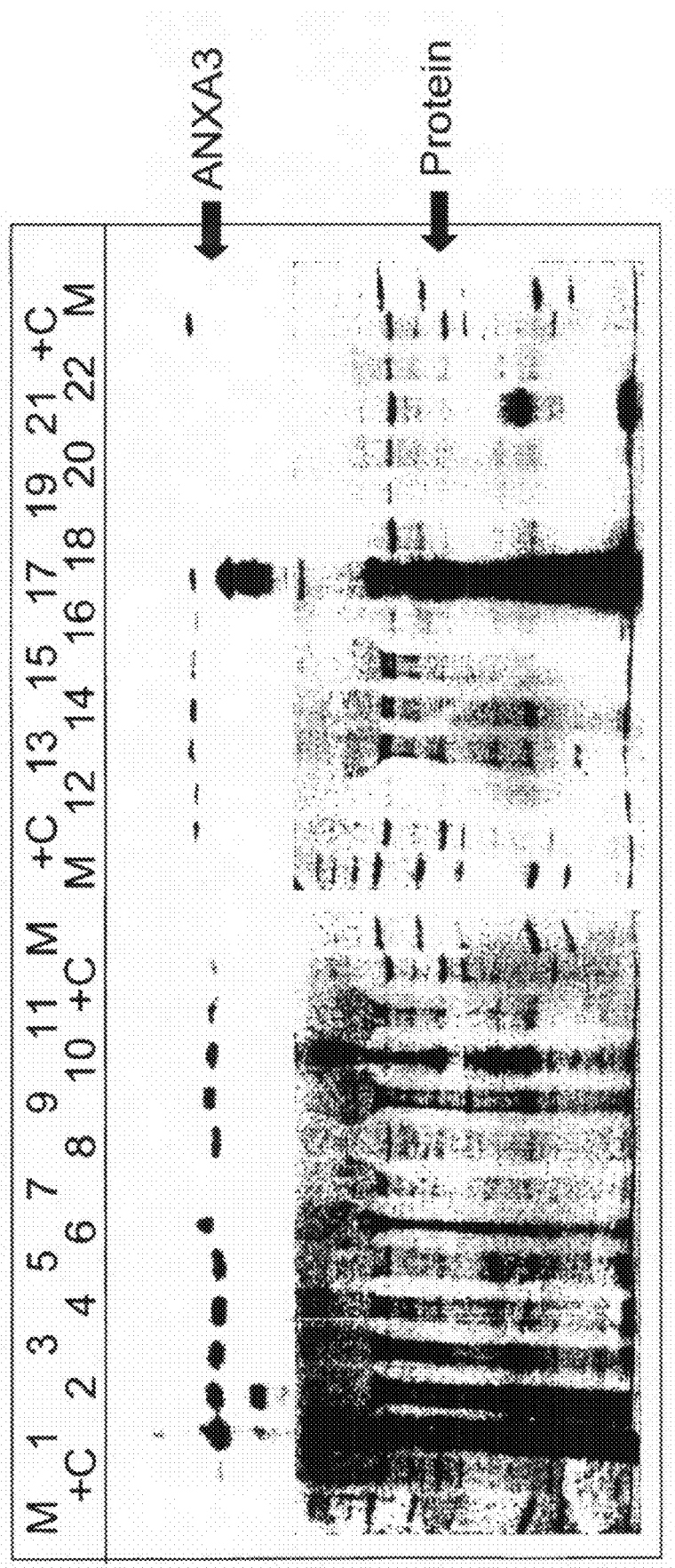
FIG. 4: Western blot quantification of annexin A3 in exprimate pellets of urine obtained after prostatic massage of BPH patients. Other details follow FIG. 3.
Figure 5:
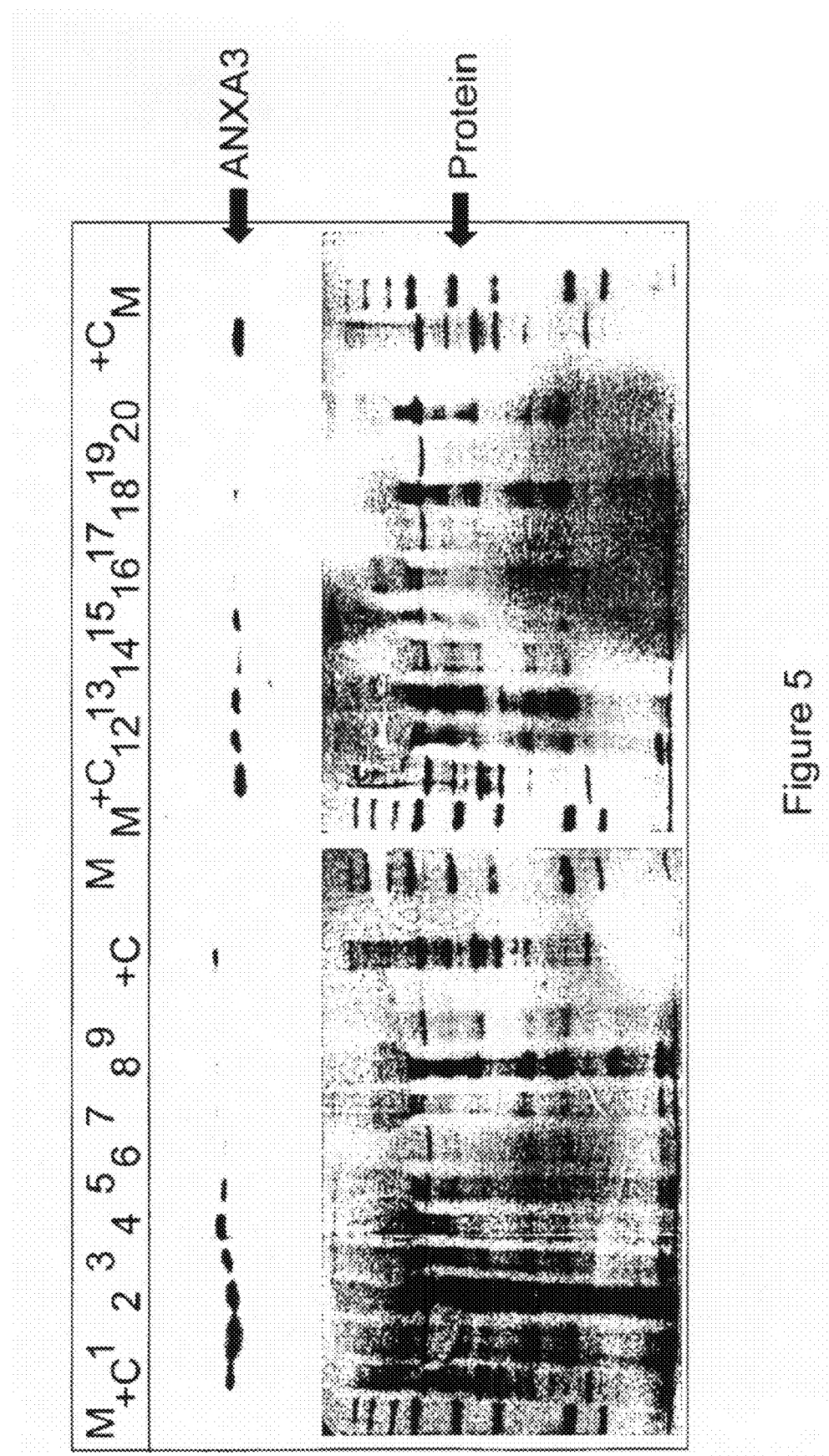
FIG. 5: Western blot quantification of annexin A3 in exprimate pellet of urine obtained after prostatic massage of non-cancer control patients. Other details follow FIG. 3.
Figure 6:
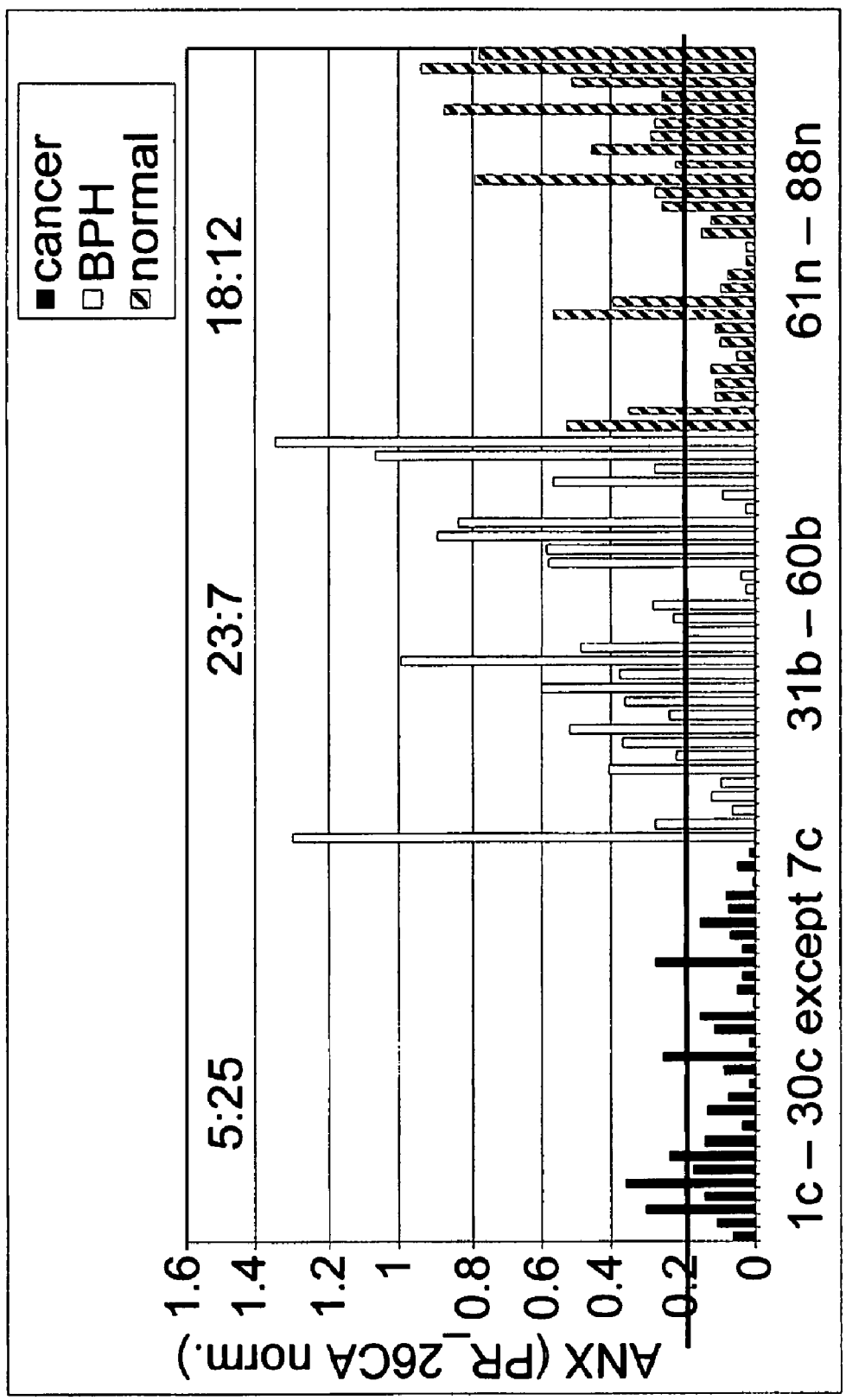
FIG. 6: Normalized annexin A3 signals from cell pellets of urine of patients following prostate massage as shown in FIG. 3 to FIG. 5. Annexin A3 values from different gels are normalized in arbitrary units of 7.5 µg of total cell protein lysate from a prostate tumor (PR-26CA) containing annexin A3 as a positive control in each of FIG. 3 to FIG. 5.

Examples of protein analysis of exprimate massaged prostate urine cell pellets from patients diagnosed with cancer, benign prostatic hyperplasia (BPH) or control patients with conditions diagnosed as unrelated to cancer are shown in FIGS. 3-5, respectively. The top panels in each of FIGS. 3 to FIG. 5 show annexin A3 enhanced chemiluminescence (ECL) signal from western blot, and the bottom panels show the entire loaded protein signal as stained with Ponceau S ('Protein'). Each gel contains a molecular weight ladder (M) as well as duplicates of 7.5 µg of total cell protein lysate from a prostate tumor containing annexin A3 as a positive control (+C). Annexin A3 signals from samples on different gels can be compared by normalization to the average value of the replicate respective positive controls. We found in a preliminary study that the pellets of exprimate urine samples of cancer patients have much less annexin A3 than either benign prostatic hyperplasia (BPH) patients or healthy control patients (FIG. 6). For instance, regarding the reference value of 0.2-fold the amount of annexin A3 signal (abundance) as in PR __26CA, only 5/30 (5:25) exprimate urine samples of cancer patients have more than 0.2 fold the reference value, while 23/30 (23:7) of the exprimate urine samples of BPH patients and 18/30 (18:12) of the exprimate urine samples of healthy control patients exceeded this reference value. These results show that on average, those cell pellets from samples of exprimate urine of cancer patients contain less annexin A3 than samples of exprimate urine from BPH patients or healthy control patients.

The supernatants resulting from the separation process of the urine samples, in particular of exprimate urine samples, and fractions thereof may be used to determine the extracellular abundance of at least one annexin protein, preferably of annexin A3.

It is particularly preferred to use the supernatants for diagnosing cancer, in particular, of the urogenital and/or intestinal tract and/or for discrimination between cancerous and non-cancerous tissue.

A cation chelator, especially a $Ca^{2+}$-chelator, particularly EDTA and/or EGTA, may be added to the urine sample or fraction thereof prior to determining the abundance of at least one annexin protein, preferably of annexin A3. The addition of the cation chelator may occur prior to subjection of the samples or fractions thereof to the separating process.

Preferably, determination of the abundance of at least one extracellular annexin protein, particularly annexin of A3, is performed in an cation chelator treated, particularly EDTA and/or EGTA treated, supernatant and for comparison in a supernatant lacking a cation chelator, particularly EDTA and/or EGTA. The supernatant is preferably derived from the same urine sample, in particular exprimate urine sample, or a fraction thereof.

Based on the reasoning that in particular annexin A3 translocation from the interior to the exterior of cells is differentially affected during the development of prostate cancer, we include the determination of whether there is any difference in the intracellular/extracellular localisation of annexin A3 in assocation with cancer. The extracellular environment as already mentioned is understood as the extracellular space including the outer surface of plasma membranes of cells. Exprimate urine obtained subsequent to clinical prostate massage contains cells exuded from the prostate. As well as the possibility of extracellular annexin A3 in exosomes, free annexin A3 could bind to negatively charged groups such as phospholipids on the surface of cells in a calcium-dependent manner. The latter annexin A3-fraction could be released from the surface of cells into the supernatant by addition of EDTA/EGTA to the medium to chelate calcium.

A further investigation in a double-blinded, four-center study demonstrated that the ratio of total annexin A3 of pellet over supernatant was able to diagnose cases labelled fibrosis in the group of non-cancer patients. Fibrosis is associated with benign processes and indicative of non-cancer. The AUROC was 0.7072 for 'pu.anx.tot.ratio' for a total of 103 non-cancer cases. The correlation for the ratio was negative, thus increased total annexin A3 amounts in supernatants were crucial for assorting into this group. This is logic as for cancer cases a decreased annexin A3 value in supernatants was observed (see below).

The further profiling of non-cancer patients (BPH, chronic prostatitis, fibrosis, PINI-3) by ratios of annexin A3 in pellets/supematants is an important aspect for subsequent sequential and/or multiparameter steps of data analysis beyond diagnostic decision cancer vs. non-cancer.

Figure 7:
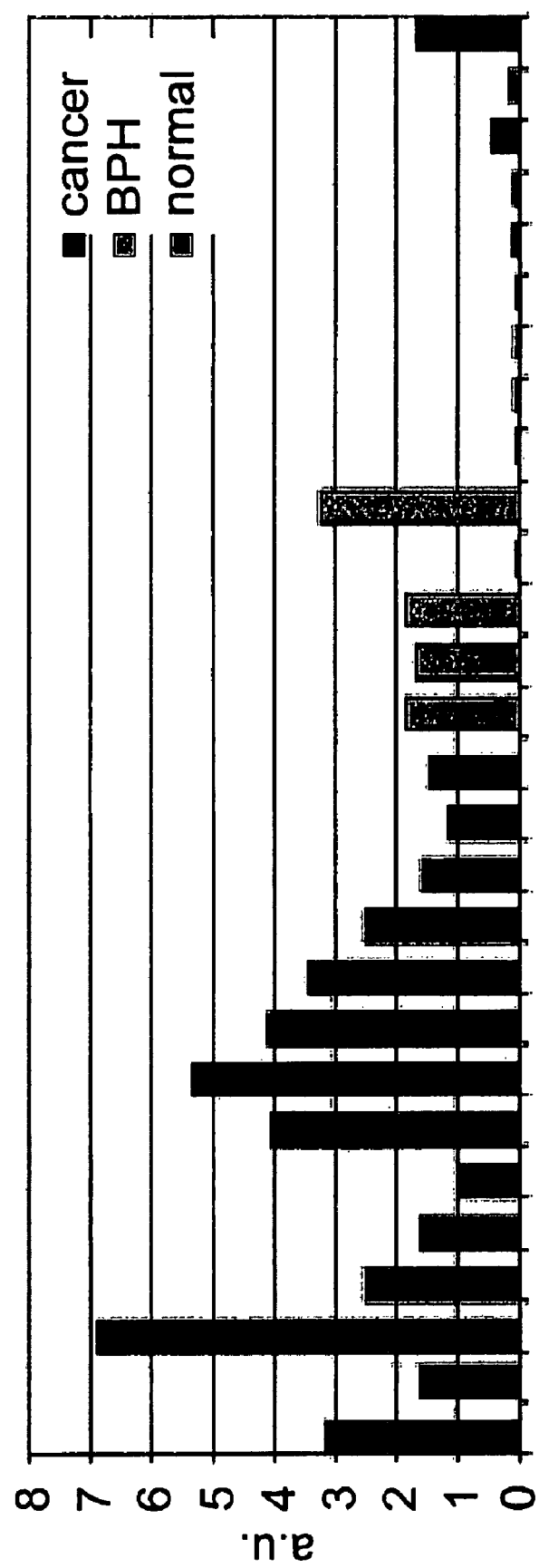
FIG. 7: Ratio of annexin A3 content between EDTA-treated supernatants and cell pellets of exprimate urine samples of patients following prostatic massage (additional patient material, not contained in FIG. 6); a.u. are arbitrary units.

Additionally, we determined annexin 3 abundances in supernatants and cell pellets of a separate independent series of patients, to compare the relative annexin A3 abundance in both cell pellets and supernatants of exprimate urine samples. Again, it was found for this different patient cohort that abundances of annexin A3 in samples of exprimate urine pellets from cancer patients are lower than abundances of annexin A3 in samples of exprimate urine pellets from BPH patients or healthy patients. Concerning the supernatants, the annexin A3 abundances from these same patients are higher in the EDTA-treated supernatants of exprimate urine samples of cancer patients than in EDTA-treated supernatants of exprimate urine samples of BPH patients or healthy patients. From individual ratios of extracellular (EDTA-treated supernatants) and intracellular (1000×g pellets) fractions of exprimate urine an even clearer image emerged, as shown in FIG. 7. Taken together, these data indicate false positive rates around or below 10% and moreover the ratios of annexin A3 expression in supernatants (annexin A3-S) vs. pellets (annexin A3-P) allows a discrimination of cancer vs. BPH vs. controls as shown in Table 1: essentially annexin A3-S is high in cancer and BPH, and low in controls, whereas annexin A3-P is high in BPH and controls and low in cancer; thus having high S (or S/P), low P for cancer; high S (or S/P) and high P for BPH; and low S (or S/P) and high P for controls; individual ratios (S/P) give clearest picture as compared to pellets alone (FIG. 7). Additional calibration for protein abundances further improves the picture.

The abundance of at least one annexin protein, preferably annexin A3, may be determined by immunohistochemical methods, in particular using tissue samples, such as tissue sections.

We also use at least one anti-annexin antibody, in particular of anti-annexin A3 antibody, for diagnosis of cancer, in particular of the urogenital and/or intestinal tract, and/or for discrimination between cancerous and non-cancerous tissue. The anti-annexin antibody may be used for pathohistological-diagnostically staining of tissue samples, in particular tissue sections. The samples may be obtained by biopsies or complete tissue excision. In particular, the tissue samples to be stained by the anti-annexin antibody are derived from prostate biopsies or prostate tissue after protectomy.

A polyclonal rabbit serum containing antibodies against annexin A3 was obtained and used to localize annexin A3 in prostate tissues by immune histochemistry. Because of the large number of annexin family members, we characterized the specificity of the anti-annexin A3 polyclonal antibody by Western blot prior to immune histochemistry. The vast majority of the signal obtained by Western blot of prostate benign and cancer tissue cell lysates comes from annexin A3 (FIG. 1). A marginal abundance of signal was observed for higher molecular weight protein, which is presumably annexin A6. This antibody produced a strong clean band using approximately 120 ng recombinant 60 kDa GST(Glutathione-S-Transferase)-annexin A3 under the same conditions. A thorough quantification, based on radioactive values from 2D gels from biopsies, protein stains of 1D and 2D gels and 1D and 2D Western blots from biopsies and exprimate urines, lead to determination of detection limits of protein concentrations in exprimate urine samples ranging from 0.02 to >15 ng/ml. The limit of detection was somewhere below but near to 0.01 ng/ml. In terms of protein content the range is from 0.001 to more than 0.3 ng/µg total protein.

Figure 2:
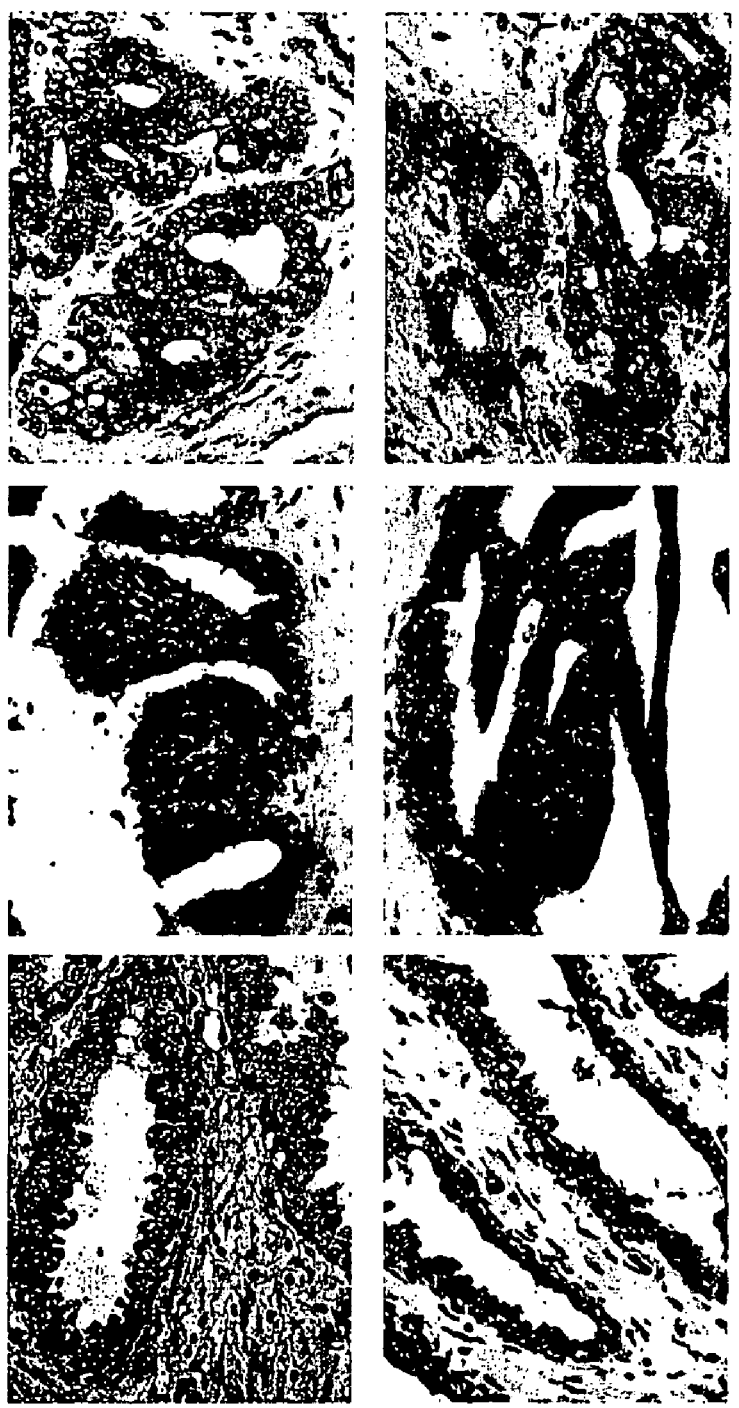
FIG. 2: Immune histochemistry of Annexin 3: annexin A3 immunoreactivity of the anti-annexin A3 polyclonal serum (dilution: 1:100) was found in the epithelial cells of A) benign prostate tissue. In B) cribbriform prostatic intraepithelial neoplasis (PIN) and C) cancer tissue, epithelial and cancer cells were stained. An elevated level of diffuse extra-epithelial localisation was also observed. Brown color indicates annexin A3-specific peroxidase staining. Blue color represents counter staining of the tissue with Gill's hematoxylin solution (Sigma).

It is therefore probable that this antibody recognizes predominantly annexin A3 in immune histochemistry, as shown in FIG. 2, where the corresponding annexin A3 signal is restricted to epithelial cells in healthy prostate, and additionally to cancerous cells in tumors. Stromal cells exhibited enhanced staining in early cancer. The rationale of mechanism for differences of annexin A3 in prostate cancer and BPH tissue tentatively indicates a transition from intracellular, more localized and in total lower expression to extracellular and in total higher expression when compared to controls.

The distribution of annexin A3 staining was suggestive of cytoplasmic and membrane localisation (FIG. 2), although the overall level of staining in individual cells seemed lower in cancer than benign tissue (FIG. 2), the overall level of annexin A3 in the same cancer tissue was higher (e.g., FIG. 1), which may be explained by more annexin A3-containing cells in cancerous tissue, and/or more extracellular annexin A3 in cancerous tissue.

In a comprehensive study (four centers, double-blinded) taking into account and measuring for the first time total annexin amounts in supernatants and pellets of exprimate urine of 250 patients and moreover quantifying the potential contribution of neutrophils to the annexin A3 signal (by parallel quantification of neutrophil marker NGAL), it was observed that annexin A3 levels were reduced in the supernatants of exprimate urine of patients with cancer. In general terms, this result indicates, that higher levels of annexin A3 are observed in exprimate urine of non-cancer patients with fibrosis/BPH, than cancer patients. However, these levels were much reduced to negligible in non-exprimate conventional urine. Therefore, it is concluded that the annexin A3 measured in exprimate urine originates predominantly in the prostate, and is released into the urine as a consequence of the prostatic massage process. It has been shown above that annexin A3 is expressed primarily in the ductal epithelial cells of the healthy prostate. For discrimination of cancer vs. non-cancer alone, the data indicate that amount of annexin A3 in supernatants has the biggest diagnostic value (AUROC-values for a combined readout of annexin A3 per µg protein and total annexin A3 in supernatants of exprimate urine of prostate cancer patients with initial PSA-values between 4-10 were 0.78-0.82). It was observed a disturbance of pellet-annexin A3 in case of higher NGAL-values; so corresponding AUROC's for pellet annexin A3 were in the range of 0.55-0.65).

It is also known that in a prostate with cancer, only a small percentage of the epithelial ductal cells are cancerous. Therefore, the measured differences in extra-cellular annexin A3 abundance should be non-significant according to logical reasoning. Nevertheless, a considerable and significant reduction of average annexin A3 abundance in the exprimate urine of cancer patients relative to non-cancerous patients was observed. It is not possible to rationalize why this should be the case because the non-cancerous epithelial cells should continue to secrete annexin A3 according to intuitive conventional wisdom. Possibly, the presence of cancer causes the secretion of a trans-acting substance, such as cytokine, that affects the annexin A3 secretion from the bulk of epithelial cell in a prostate with a cancerous lesion. It is unclear whether this trans-acting factor originates in the cancerous cells themselves, or in other cells. It is well documented that trans-acting factors influence the relationship between cancerous cell and their mesenchymal/stromal environment, and vice versa. Irrespective of the mechanim(s) responsible, our empirical observations are unambiguous, and clearly but surprisingly demonstrate that lower levels of annexin A3 in the exprimate urine provide a predictive measure of the probability that the patient has tumorous cells in the prostate. This diagnostic use of annexin A3 levels in exprimate urine can be combined with other diagnostic indexes, such as the level of prostate specific antigen (PSA), as demonstrated by way of example. These results also suggest that the presence of the annexin A3 protein is associated with the healthy phenotype.

Therefore, annexin A3 protein can be applied in a therapeutic manner to treat cancer, by enhancing the levels of extracellular annexin A3.

The mechanisms underlying the observed results are under investigation, and they potentially reflect a transition of some kind of completely healthy prostate epithelium proceeding to a non-cancerous stage (fibrosis/BPH) which is associated with elevated levels of annexin A3 in both pellets and supernatants of exprimate urine, with the above ratio of total annexin A3 (p/s) with highest diagnostic value. In cancer, there is a clear and surprising correlation to decreased annexin A3 amounts in supernatants of exprimate urine of cancer patients; pellet annexin A3 amounts appear to have a contaminating contribution by NGAL-positive leukocytes/neutrophils.

It is thus highly desirable to measure annexin A3 levels in both pellet and supernatant. This information on the protein level is not accessible by genomic methods e.g., as superficially insinuated but not substantiated by US2003/0108963A1.

In summary, annexin A3 exhibited predominantly intracellular staining in healthy tissue, and extra-epithelial location in early cancerous tissue: with advanced cancer exhibiting markedly reduced annexin A3 staining within cancer cells.

The urine samples or fractions thereof may be obtained from urine, in particular from exprimate urine, which is recovered subsequent to prostate massage, particularly by rectal finger insertion.

The urine samples or fractions thereof may be purified, particularly are freed from neuirophils, monocytes or peripheral blood mononuclear cells (PMBCs), especially by means of magneto beads. Preferably, samples or fractions thereof of morning urine are used.

Annexin levels may be measured in faeces or epithelial cells of the intestinal tract. Further, annexin levels can be used to treat and/or to diagnose epithelial cancers of gastrointestinal tract in any fraction or preparation of faeces (any potentially exosome-producing epithelial surface). Annexin levels are used further to treat and/or to diagnose colorectal cancer. The methods can be combined with a determination of neutrophils, in particular of calprotectin and/or neutrophil gelatinase-associated lipocalin (NGAL), to discriminate inflammatory conditions (Crohn's disease or colitis ulcerosa from cancer).

At least one annexin protein, preferably annexin A3 and/or annexin A8, in particular annexin A3, can be used as diagnostic marker and/or therapeutic target for diseases disclosed in the description, in particular for prostate cancer, colorectal cancer and/or osteoporosis, preferably for subgroups thereof.

It is possible to treat cancer, in particular, of the urogenital and/or intestinal tract. This is preferably achieved by the enhancement of the in vivo abundance of at least one annexin protein, for instance of at least one extracellular annexin.

Furthermore, we can diagnose cancer, in particular of the urogenital and/or intestinal tract, and/or the discrimination between cancerous and non-cancerous tissue. This is particularly achieved by the determination of the ratios of intra- versus extracellular abundances and extra-versus intracellular abundances respectively of annexin proteins which may be, if appropriate, combined with the determination of the corresponding ratios for other proteins. Preferably, diagnosis of cancer and/or discrimination between cancerous and non-cancerous tissue is based on the extracellular abundance of at least one annexin protein. The determined protein ratios and abundances respectively reveal differences between cancerous and non-cancerous tissues, thus allowing for a patient's profiling. Therefore, annexin proteins, in particular annexin A3, are reliable diagnostic markers that may even completely substitute tumor markers that are conventionally applied in cancer diagnosis.

For a more detailed description, reference will now be made to the accompanying tables and figures:

TABLE 1

Table 1: Summary of diagnostic results, annexin A3 abundances are low in pellets (annexin A3-P) of exprimate urine samples of cancer patients and comparatively high in corresponding pellets of exprimate urine samples of BPH patients and healthy patients. For annexin A3 abundances in supernatants (annexin A3-S) of exprimate urine samples, there is a different picture: they are low for healthy patients and high for cancer and BPH patients. The combined read-out correctly assorts the three cases with numbers indicated in the lower part of the table. Concerning further details it is referred to the above specification.

| # of samples | Cancer 40 | BPH 40 | Controls 40 | False neg (% of 120) | False pos (% of 120) |
|---|---|---|---|---|---|
| ANXA3-P (% of 40) | | | | | |
| Biomarker down | 84 | 23 | 40 | | |
| Biomarker up | 16 | 77 | 60 | 6 | 13.3 |
| ANXA3-S (% of 40) | | | | | |
| Biomarker down | 5 | 20 | 91 | | |
| Biomarker up | 95 | 80 | 9 | | |
| Ratio ANXA3-S/ ANXA3-P and sorting | | | | | |
| Cancer | 92 | 12 | 3 | | |
| BPH | 6 | 80 | 6 | 1.5 | 7.5 |
| Control | 2 | 8 | 91 | | |

TABLE 2

Table 2: Protein parameters measured from exprimate urine supernatant and pellets fractions.

| Name | Description |
|---|---|
| P_ug_tot | Pellet: Total Protein amount (μg) |
| U_ug_tot | Supernatant*: Total Protein amount (μg) |
| P_ANX_ug | Pellet: Annexin signal level per μg protein |
| P_ANX_tot | Pellet: Annexin signal level per total patient sample |
| U_ANX_ug | Supernatant: Annexin signal level per μg protein |
| U_ANX_tot | Supernatant: Annexin signal level per total patient sample |
| PU_ANX_ug | Pellet + Supernatant: Annexin-level per μg protein |
| PU_ANX_tot | Pellet + Supernatant: Annexin-level per total patient sample |
| PU_ANX_ug_ratio | Ratio of Pellet/Supernatant: Annexin level per ug protein |

TABLE 2-continued

Table 2: Protein parameters measured from exprimate urine supernatant and pellets fractions.

| Name | Description |
| --- | --- |
| PU_ANX_tot_ratio | Ratio Pellet/Supernatant: Annexin level per total patient sample |
| P_NGAL_ug | Pellet: NGAL signal level per μg protein |
| P_NGAL_tot | Pellet: NGAL signal level per total patient sample |
| U_NGAL_ug | Supernatant: NGAL signal level per μg protein |
| U_NGAL_tot | Supernatant: NGAL signal level per total patient sample |
| PU_NGAL_ug | Pellet + Supernatant: NGAL-level per μg protein |
| PU_NGAL_tot | Pellet + Supernatant: NGAL-level per total patient sample |
| PU_NGAL_ug_ratio | Ratio of Pellet/Supernatant: NGAL level per ug protein |
| PU_NGAL_tot_ratio | Ratio Pellet/Supernatant: NGAL level per total patient sample |
| P_ANX_NGAL_ug_ratio | Pellet: Annexin/NGAL ratio per μg protein |
| U_ANX_NGAL_ug_ratio | Supernatant: Annexin/NGAL ratio per μg protein |
| PU_ANX_NGAL_ug_ratio | Pellet + Supernatant: Annexin/NGAL ratio per μg protein |

('U' = 'supernatant')

TABLE 3

Table 3: description of abbreviations and variables used in example 4.

| Variable | Description |
| --- | --- |
| P.ug.tot | Pellet: Total Protein Quantity (μg) |
| U.ug.tot | Supernatant: Total Protein Quantity (μg) |
| P.ANX.ug | Pellet: Annexin-Level per μg Protein |
| P.ANX.tot | Pellet: Annexin-Level per total Sample |
| U.ANX.ug | Supernatant: Annexin-Level per μg Protein |
| U.ANX.tot | Supernatant: Annexin-Level per total Sample |
| PU.ANX.ug | Supernatant + Pellet: Annexin-Level per μg Protein |
| PU.ANX.tot | Supernatant + Pellet: Annexin-Level per total Sample |
| PU.ANX.ug.ratio | Ratio Pellet/Supernatant: Annexin Level per ug Protein |
| PU.ANX.tot.ratio | Ratio Pellet/Supernatant: Annexin Level per total Sample |
| psa.ini | Blood PSA levels |
| perc.free.psa | Percentage free PSA |

TABLE 4

Table 4: ROC curve analysis results for the indicated variable parameters (see Table 3 for description), performed for patients grouped according to PSA values of 4-10 ng/mL. The test parameters, resulting AUROC values, and number of patients included per analysis are tabularized.

| Test | AUROC | Patients |
| --- | --- | --- |
| anx.comb.var | 0.78 | 112 |
| comb.var.anx.psa 1 | 0.76 | 112 |
| u.anx.tot | 0.76 | 112 |
| pu.anx.tot | 0.75 | 112 |
| u.anx.ug | 0.74 | 112 |
| perc.free.psa | 0.72 | 103 |
| psa.ini | 0.57 | 109 |

TABLE 5

Table 5: ROC curve analysis results for the indicated variable parameters (see Table 3 for description), performed for patients grouped according to PSA values 2-6 ng/mL. The test parameters, resulting AUROC values, and number of patients included per analysis are tabularized.

| Test | AUROC | Patients |
| --- | --- | --- |
| comb.var.anx.psa 2 | 0.79 | 109 |
| comb.var.anx.psa 1 | 0.77 | 109 |
| pu.anx.tot | 0.73 | 109 |
| anx.comb.var | 0.71 | 109 |
| u.anx.tot | 0.71 | 109 |
| pu.anx.ug | 0.71 | 109 |
| u.anx. | 0.71 | 109 |
| p.anx.tot | 0.69 | 109 |
| psa.ini | 0.69 | 109 |
| perc.free.psa | 0.69 | 109 |

TABLE 6

Table 6: ROC curve analysis results for the indicated variable parameters (see Table 3 for description), performed for all patients, including all PSA values. The test parameters, resulting AUROC values, and number of patients included per analysis are tabularized.

| Test | AUROC | Patients |
| --- | --- | --- |
| comb.var.anx.psa 1 | 0.75 | 226 |
| comb.var.anx.psa 2 | 0.73 | 244 |
| perc.free.psa | 0.70 | 227 |
| psa.ini | 0.68 | 239 |
| anx.comb.var | 0.67 | 244 |
| pu.anx.tot | 0.66 | 245 |

TABLE 7

Table 7: Data corresponding to the ROC curve of FIG. 9. The maximum likelihoods estimate model is described in Tables 8 and 9.

| Criterion | Sens. (95% C.I.) | Spec. (95% C.I.) | +LR | −LR | +PV | −PV |
| --- | --- | --- | --- | --- | --- | --- |
| >=−3.5155 | 100.0 (93.7-100.0) | 0.0 (0.0-6.9) | 1.00 |  | 52.3 |  |
| >−3.5155 | 98.2 (90.6-99.7) | 0.0 (0.0-6.9) | 0.98 |  | 51.9 | 0.0 |
| >−2.6907 | 98.2 (90.6-99.7) | 1.9 (0.3-10.3) | 1.00 | 0.91 | 52.3 | 50.0 |
| >−2.5444 | 98.2 (90.6-99.7) | 3.8 (0.6-13.2) | 1.02 | 0.46 | 52.8 | 66.7 |
| >−2.0663 | 98.2 (90.6-99.7) | 5.8 (1.3-16.0) | 1.04 | 0.30 | 53.3 | 75.0 |
| >−1.9579 | 98.2 (90.6-99.7) | 7.7 (2.2-18.6) | 1.06 | 0.23 | 53.8 | 80.0 |
| >−1.9096 | 98.2 (90.6-99.7) | 9.6 (3.2-21.0) | 1.09 | 0.18 | 54.4 | 83.3 |

TABLE 7-continued

Table 7: Data corresponding to the ROC curve of FIG. 9. The maximum likelihoods estimate model is described in Tables 8 and 9.

| Criterion | Sens. (95% C.I.) | Spec. (95% C.I.) | +LR | −LR | +PV | −PV |
|---|---|---|---|---|---|---|
| >−1.6827 | 98.2 (90.6-99.7) | 11.5 (4.4-23.5) | 1.11 | 0.15 | 54.9 | 85.7 |
| >−1.6673 | 98.2 (90.6-99.7) | 13.5 (5.6-25.8) | 1.14 | 0.13 | 55.4 | 87.5 |
| >−1.5429 | 96.5 (87.9-99.5) | 13.5 (5.6-25.8) | 1.12 | 0.26 | 55.0 | 77.8 |
| >−1.4419 | 96.5 (87.9-99.5) | 15.4 (6.9-28.1) | 1.14 | 0.23 | 55.6 | 80.0 |
| >−1.3903 | 94.7 (85.4-98.8) | 15.4 (6.9-28.1) | 1.12 | 0.34 | 55.1 | 72.7 |
| >−1.273 | 94.7 (85.4-98.8) | 17.3 (8.3-30.3) | 1.15 | 0.30 | 55.7 | 75.0 |
| >−1.2619 | 94.7 (85.4-98.8) | 19.2 (9.6-32.5) | 1.17 | 0.27 | 56.2 | 76.9 |
| >−1.1825 | 93.0 (83.0-98.0) | 19.2 (9.6-32.5) | 1.15 | 0.36 | 55.8 | 71.4 |
| >−1.1791 | 93.0 (83.0-98.0) | 21.2 (11.1-34.7) | 1.18 | 0.33 | 56.4 | 73.3 |
| >−1.0689 | 91.2 (80.7-97.1) | 21.2 (11.1-34.7) | 1.16 | 0.41 | 55.9 | 68.7 |
| >−1.0621 | 91.2 (80.7-97.1) | 23.1 (12.5-36.8) | 1.19 | 0.38 | 56.5 | 70.6 |
| >−1.0192 | 91.2 (80.7-97.1) | 25.0 (14.0-38.9) | 1.22 | 0.35 | 57.1 | 72.2 |
| >−1.0041 | 91.2 (80.7-97.1) | 26.9 (15.6-41.0) | 1.25 | 0.33 | 57.8 | 73.7 |
| >−0.9502 | 91.2 (80.7-97.1) | 28.8 (17.1-43.1) | 1.28 | 0.30 | 58.4 | 75.0 |
| >−0.8458 | 89.5 (78.5-96.0) | 28.8 (17.1-43.1) | 1.26 | 0.36 | 58.0 | 71.4 |
| >−0.8339 | 89.5 (78.5-96.0) | 30.8 (18.7-45.1) | 1.29 | 0.34 | 58.6 | 72.7 |
| >−0.8285 | 87.7 (76.3-94.9) | 30.8 (18.7-45.1) | 1.27 | 0.40 | 58.1 | 69.6 |
| >−0.8253 | 87.7 (76.3-94.9) | 32.7 (20.3-47.1) | 1.30 | 0.38 | 58.8 | 70.8 |
| >−0.8237 | 87.7 (76.3-94.9) | 34.6 (22.0-49.1) | 1.34 | 0.35 | 59.5 | 72.0 |
| >−0.8044 | 87.7 (76.3-94.9) | 36.5 (23.6-51.0) | 1.38 | 0.34 | 60.2 | 73.1 |
| >−0.7935 | 87.7 (76.3-94.9) | 38.5 (25.3-53.0) | 1.43 | 0.32 | 61.0 | 74.1 |
| >−0.7836 | 87.7 (76.3-94.9) | 40.4 (27.0-54.9) | 1.47 | 0.30 | 61.7 | 75.0 |
| >−0.7431 | 87.7 (76.3-94.9) | 42.3 (28.7-56.8) | 1.52 | 0.29 | 62.5 | 75.9 |
| >−0.7371 | 86.0 (74.2-93.7) | 42.3 (28.7-56.8) | 1.49 | 0.33 | 62.0 | 73.3 |
| >−0.6841 | 86.0 (74.2-93.7) | 44.2 (30.5-58.7) | 1.54 | 0.32 | 62.8 | 74.2 |
| >−0.6759 | 86.0 (74.2-93.7) | 46.2 (32.2-60.5) | 1.60 | 0.30 | 63.6 | 75.0 |
| >−0.6297 | 86.0 (74.2-93.7) | 48.1 (34.0-62.4) | 1.66 | 0.29 | 64.5 | 75.8 |
| >−0.6205 | 86.0 (74.2-93.7) | 50.0 (35.8-64.2) | 1.72 | 0.28 | 65.3 | 76.5 |
| >−0.6095 | 86.0 (74.2-93.7) | 51.9 (37.6-66.0) | 1.79 | 0.27 | 66.2 | 77.1 |
| >−0.5341 | 86.0 (74.2-93.7) | 53.8 (39.5-67.8) | 1.86 | 0.26 | 67.1 | 77.8 |
| >−0.5077 | 86.0 (74.2-93.7) | 55.8 (41.3-69.5) | 1.94 | 0.25 | 68.1 | 78.4 |
| >−0.503 | 86.0 (74.2-93.7) | 57.7 (43.2-71.3) | 2.03 | 0.24 | 69.0 | 78.9 |
| >−0.4942 | 86.0 (74.2-93.7) | 59.6 (45.1-73.0) | 2.13 | 0.24 | 70.0 | 79.5 |
| >−0.4548 | 84.2 (72.1-92.5) | 59.6 (45.1-73.0) | 2.09 | 0.26 | 69.6 | 77.5 |
| >−0.4346 | 82.5 (70.1-91.2) | 59.6 (45.1-73.0) | 2.04 | 0.29 | 69.1 | 75.6 |
| >−0.4211 | 80.7 (68.1-89.9) | 59.6 (45.1-73.0) | 2.00 | 0.32 | 68.7 | 73.8 |
| >−0.3763 | 78.9 (66.1-88.6) | 59.6 (45.1-73.0) | 1.95 | 0.35 | 68.2 | 72.1 |
| >−0.201 | 78.9 (66.1-88.6) | 61.5 (47.0-74.7) | 2.05 | 0.34 | 69.2 | 72.7 |
| >−0.1764 | 78.9 (66.1-88.6) | 63.5 (49.0-76.4) | 2.16 | 0.33 | 70.3 | 73.3 |
| >−0.1476 | 78.9 (66.1-88.6) | 65.4 (50.9-78.0) | 2.28 | 0.32 | 71.4 | 73.9 |
| >−0.1049 | 77.2 (64.2-87.2) | 65.4 (50.9-78.0) | 2.23 | 0.35 | 71.0 | 72.3 |
| >−0.0809 | 75.4 (62.2-85.9) | 65.4 (50.9-78.0) | 2.18 | 0.38 | 70.5 | 70.8 |
| >−0.0773 | 75.4 (62.2-85.9) | 67.3 (52.9-79.7) | 2.31 | 0.36 | 71.7 | 71.4 |
| >−0.0323 | 73.7 (60.3-84.5) | 67.3 (52.9-79.7) | 2.25 | 0.39 | 71.2 | 70.0 |
| >−0.0007 | 71.9 (58.5-83.0) | 67.3 (52.9-79.7) | 2.20 | 0.42 | 70.7 | 68.6 |
| >0.007 | 71.9 (58.5-83.0) | 69.2 (54.9-81.3) | 2.34 | 0.41 | 71.9 | 69.2 |
| >0.0841 | 70.2 (56.6-81.6) | 69.2 (54.9-81.3) | 2.28 | 0.43 | 71.4 | 67.9 |
| >0.085 | 68.4 (54.8-80.1) | 69.2 (54.9-81.3) | 2.22 | 0.46 | 70.9 | 66.7 |
| >0.1274 | 68.4 (54.8-80.1) | 71.2 (56.9-82.9) | 2.37 | 0.44 | 72.2 | 67.3 |
| >0.1395 | 68.4 (54.8-80.1) | 73.1 (59.0-84.4) | 2.54 | 0.43 | 73.6 | 67.9 |
| >0.1475 | 68.4 (54.8-80.1) | 75.0 (61.1-86.0) | 2.74 | 0.42 | 75.0 | 68.4 |
| >0.1672 | 68.4 (54.8-80.1) | 76.9 (63.2-87.5) | 2.96 | 0.41 | 76.5 | 69.0 |
| >0.1764 | 68.4 (54.8-80.1) | 78.8 (65.3-88.9) | 3.23 | 0.40 | 78.0 | 69.5 |
| >0.1803 | 68.4 (54.8-80.1) | 80.8 (67.5-90.4) | 3.56 | 0.39 | 79.6 | 70.0 |
| >0.1808 | 66.7 (52.9-78.6) | 80.8 (67.5-90.4) | 3.47 | 0.41 | 79.2 | 68.9 |
| >0.2017 | 64.9 (51.1-77.1) | 80.8 (67.5-90.4) | 3.38 | 0.43 | 78.7 | 67.7 |
| >0.2682 | 63.2 (49.3-75.5) | 80.8 (67.5-90.4) | 3.28 | 0.46 | 78.3 | 66.7 |
| >0.2761 | 63.2 (49.3-75.5) | 82.7 (69.7-91.7) | 3.65 | 0.45 | 80.0 | 67.2 |
| >0.3249 | 61.4 (47.6-74.0) | 82.7 (69.7-91.7) | 3.55 | 0.47 | 79.5 | 66.2 |
| >0.3445 | 59.6 (45.8-72.4) | 82.7 (69.7-91.7) | 3.45 | 0.49 | 79.1 | 65.2 |
| >0.4091 | 57.9 (44.1-70.9) | 82.7 (69.7-91.7) | 3.35 | 0.51 | 78.6 | 64.2 |
| >0.476 | 57.9 (44.1-70.9) | 84.6 (71.9-93.1) | 3.76 | 0.50 | 80.5 | 64.7 |
| >0.4824 | 57.9 (44.1-70.9) | 86.5 (74.2-94.4) | 4.30 | 0.49 | 82.5 | 65.2 |
| >0.4969 | 57.9 (44.1-70.9) | 88.5 (76.5-95.6) | 5.02 | 0.48 | 84.6 | 65.7 |
| >0.5666 | 57.9 (44.1-70.9) | 90.4 (79.0-96.8) | 6.02 | 0.47 | 86.8 | 66.2 |
| >0.6639 | 57.9 (44.1-70.9) | 92.3 (81.4-97.8) | 7.53 | 0.46 | 89.2 | 66.7 |
| >0.683 | 56.1 (42.4-69.3) | 92.3 (81.4-97.8) | 7.30 | 0.48 | 88.9 | 65.8 |
| >0.6877 | 56.1 (42.4-69.3) | 94.2 (84.0-98.7) | 9.73 | 0.47 | 91.4 | 66.2 |
| >0.6934 | 54.4 (40.7-67.6) | 94.2 (84.0-98.7) | 9.43 | 0.48 | 91.2 | 65.3 |
| >0.7038 * | 54.4 (40.7-67.6) | 96.2 (86.8-99.4) | 14.14 | 0.47 | 93.9 | 65.8 |
| >0.7226 | 52.6 (39.0-66.0) | 96.2 (86.8-99.4) | 13.68 | 0.49 | 93.8 | 64.9 |
| >0.8531 | 50.9 (37.3-64.4) | 96.2 (86.8-99.4) | 13.23 | 0.51 | 93.5 | 64.1 |
| >0.8868 | 49.1 (35.6-62.7) | 96.2 (86.8-99.4) | 12.77 | 0.53 | 93.3 | 63.3 |
| >0.9511 | 47.4 (34.0-61.0) | 96.2 (86.8-99.4) | 12.32 | 0.55 | 93.1 | 62.5 |

TABLE 7-continued

Table 7: Data corresponding to the ROC curve of FIG. 9. The maximum likelihoods estimate model is described in Tables 8 and 9.

| Criterion | Sens. (95% C.I.) | Spec. (95% C.I.) | +LR | −LR | +PV | −PV |
|---|---|---|---|---|---|---|
| >0.9527 | 45.6 (32.4-59.3) | 96.2 (86.8-99.4) | 11.86 | 0.57 | 92.9 | 61.7 |
| >1.0734 | 43.9 (30.7-57.6) | 96.2 (86.8-99.4) | 11.40 | 0.58 | 92.6 | 61.0 |
| >1.116 | 42.1 (29.1-55.9) | 96.2 (86.8-99.4) | 10.95 | 0.60 | 92.3 | 60.2 |
| >1.1278 | 40.4 (27.6-54.2) | 96.2 (86.8-99.4) | 10.49 | 0.62 | 92.0 | 59.5 |
| >1.1707 | 38.6 (26.0-52.4) | 96.2 (86.8-99.4) | 10.04 | 0.64 | 91.7 | 58.8 |
| >1.1763 | 36.8 (24.5-50.7) | 96.2 (86.8-99.4) | 9.58 | 0.66 | 91.3 | 58.1 |
| >1.2415 | 35.1 (22.9-48.9) | 96.2 (86.8-99.4) | 9.12 | 0.68 | 90.9 | 57.5 |
| >1.267 | 33.3 (21.4-47.1) | 96.2 (86.8-99.4) | 8.67 | 0.69 | 90.5 | 56.8 |
| >1.3195 | 31.6 (19.9-45.2) | 96.2 (86.8-99.4) | 8.21 | 0.71 | 90.0 | 56.2 |
| >1.3976 | 29.8 (18.4-43.4) | 96.2 (86.8-99.4) | 7.75 | 0.73 | 89.5 | 55.6 |
| >1.4368 | 28.1 (17.0-41.5) | 96.2 (86.8-99.4) | 7.30 | 0.75 | 88.9 | 54.9 |
| >1.4579 | 26.3 (15.5-39.7) | 96.2 (86.8-99.4) | 6.84 | 0.77 | 88.2 | 54.3 |
| >1.4781 | 24.6 (14.1-37.8) | 96.2 (86.8-99.4) | 6.39 | 0.78 | 87.5 | 53.8 |
| >1.6158 | 22.8 (12.8-35.8) | 96.2 (86.8-99.4) | 5.93 | 0.80 | 86.7 | 53.2 |
| >1.6423 | 21.1 (11.4-33.9) | 96.2 (86.8-99.4) | 5.47 | 0.82 | 85.7 | 52.6 |
| >1.6559 | 19.3 (10.1-31.9) | 96.2 (86.8-99.4) | 5.02 | 0.84 | 84.6 | 52.1 |
| >1.7477 | 17.5 (8.8-29.9) | 96.2 (86.8-99.4) | 4.56 | 0.86 | 83.3 | 51.5 |
| >1.7524 | 17.5 (8.8-29.9) | 98.1 (89.7-99.7) | 9.12 | 0.84 | 90.9 | 52.0 |
| >1.7628 | 17.5 (8.8-29.9) | 100.0 (93.1-100.0) | | 0.82 | 100.0 | 52.5 |
| >1.8054 | 15.8 (7.5-27.9) | 100.0 (93.1-100.0) | | 0.84 | 100.0 | 52.0 |
| >1.8153 | 14.0 (6.3-25.8) | 100.0 (93.1-100.0) | | 0.86 | 100.0 | 51.5 |
| >1.8787 | 12.3 (5.1-23.7) | 100.0 (93.1-100.0) | | 0.88 | 100.0 | 51.0 |
| >2.1994 | 10.5 (4.0-21.5) | 100.0 (93.1-100.0) | | 0.89 | 100.0 | 50.5 |
| >2.4311 | 8.8 (2.9-19.3) | 100.0 (93.1-100.0) | | 0.91 | 100.0 | 50.0 |
| >2.472 | 7.0 (2.0-17.0) | 100.0 (93.1-100.0) | | 0.93 | 100.0 | 49.5 |
| >2.5544 | 5.3 (1.2-14.6) | 100.0 (93.1-100.0) | | 0.95 | 100.0 | 49.1 |
| >2.5595 | 3.5 (0.5-12.1) | 100.0 (93.1-100.0) | | 0.96 | 100.0 | 48.6 |
| >2.8088 | 1.8 (0.3-9.4) | 100.0 (93.1-100.0) | | 0.98 | 100.0 | 48.1 |
| >3.6467 | 0.0 (0.0-6.3) | 100.0 (93.1-100.0) | | 1.00 | | 47.7 |

Sens. = Sensitivity
Spec. = Specificity
+LR = Positive likelihood ratio
−LR = Negative likelihood ratio
+PV = Positive predictive value
−PV = Negative predictive value

TABLE 8

Table 8: Condensed SAS Output for the logit model which leads to comb.var.anx.psa2: Analysis of Maximum Likelihood Estimates

| Parameter | DF | Estimate | Error (Standard) | Chi-Square (Wald) | Pr > ChiSq |
|---|---|---|---|---|---|
| Intercept | 1 | −2.3860 | 1.7461 | 1.8673 | 0.1718 |
| Log PU ANX tot | 1 | −0.4747 | 0.1394 | 11.5908 | 0.0007 |
| Log PSA ini | 1 | 3.2942 | 1.0198 | 10.4343 | 0.0012 |

TABLE 9

Table 9: Condensed SAS Output for the logit model which leads to comb.var.anx.psa2: Odds Ratio Estimates

| Effect | Estimate (Point) | Confidence (95%) | Limits |
|---|---|---|---|
| log PU ANX tot | 0.622 | 0.473 | 0.818 |
| log PSA ini | 26.956 | 3.652 | 198.934 |

EXAMPLES

While our methods are described in more detail with reference to examples, those methods are by no means restricted to the examples.

Example 1

Processing of Post-prostatic Massage Urine:

Prostatic massage exprimate urine was obtained from patients undergoing clinical examination, after screening for blood prostate specific antigen (PSA) abundances had indicated elevated risk of cancer. 47 ml of urine obtained following vigorous prostate massage by rectal finger insertion was added to 3 ml 0.5 M EDTA, pH 8 precooled to 0° C., and immediately cooled to 0° C. If urine volume was <47 ml, the volume was made up with ice cooled phosphate buffered saline (PBS) solution. The cooled samples were centrifuged at 3000 rpm at 0° C. for 30 minutes to create a cell pellet. 1 ml aliquots of the supernatant were removed, frozen in liquid nitrogen, and stored at −80° C. until use. The cell pellets were gently resuspended in 2 ml ice cold PBS and transferred to Eppendorf tubes on ice, followed by centrifugation at 12000 rpm for 5 minutes at 4° C. The supernatant was removed, and the pellet frozen in liquid nitrogen and stored at −80° C. until use.

Example 2

Western Blotting:
SDS-PAGE gels for Western blotting were prepared using a BioRad-Mini gel apparatus and 12% T polyacrylamide gels with 1 mm spacers and 15 wells, according to manufacturer's instructions. Anti annexin A3 (annexin A3) was the same antibody described below. Diluted 1:20,000. Recombinant GST-annexin A3 protein was purchased from Abnova Corporation (#ABV 0040710002; Lot: T04G01-ANNEXINA3, 0.05 µg/µl, 61 kDa). Antibody binding was visualized with a goat anti-rabbit IgG (Sigma A 3937, lot #121K9151) diluted 1:1000, using the ECL detection method (Pierce) and a DIANA III CCD camera-based chemiluminescence detector (Raytest, Straubenhardt, Germany). A rabbit polyclonal serum against recombinant bacterially expressed annexin A3 exhibits primary specificity for annexin A3 and some cross reactivity for annexin A6.

Example 3

Immune Histochemistry:

Immune histochemistry was performed with 5 µm paraffin tissue sections employing polyclonal anti annexin A3 serum, according to a standard Horse Radish Peroxidase immunohistochemistry protocol using the Zymed PicTure PLUS Kit (Broad Spectrum, DAB, Zymed, South San Fransisco, Calif.). After immunostaining sections were counterstained with Gill's hematoxylin solution (Sigma).

Example

Clinical Study using Exprimate Urine of 250 Patients

Annexin A3 levels were determined in the exprimate urine of clinical patients, diagnosed as being either positive or negative for the presence of prostate cancer (PCa). A variety of additional paramters were examined, such as prostate specific antigen (PSA) levels in the blood, and other variables listed below.

Sample collection was as per example 1, but without the addition of EDTA to urine. Following prostate massage the entire exprimate urine volume was collected and recorded. A Combur-10-Test® (Roche Diagnostics Cat. No. 11 203 479) was performed immediately on an aliquot of the urine to record specific gravity, pH, Leukocyte count, and the levels of nitrite, protein, glucose, ketones, urobilinogen, bilirubin, and erythrocytes. Urine was then centrifuged at room temperature for 15 min at 1000×g. The cell pellet and supernatant of this supernatant were handled separately. After removal of the last traces of supernatant, the pellet was resuspended in 1 ml ice cold phosphate buffered saline and frozen in liquid nitrogen or on frozen $CO_2$. Separate aliquots of 2×1.8 ml and up to 2×50 ml of supernatant were similarly frozen.

Frozen protein samples were thawed, and 1/100 volumes of 2% deoxycholate were added, followed by vortexing then addition of 1/10 volume of trichloroacetic acid, vortexing, and 10 minutes incubation at 0°C. This was followed by centrifugation at 10000×g for 15 min at 4° C. to precipitate proteins. The supernatant was removed, and the pellet was washed three times with ice-cold 80% acetone by vigorously vortexing the pellet to remove remaining TCA completely, followed by recentrifugation at 10000×g as before after each wash. After the final centrifugation the supernatant was removed and the pellet was left to air dry for 2 minutes, paying attention not to completely dehydrate the pellet. The pellets were resuspended in boiling XT-sample buffer (1× XT-Buffer: 141 mM TrisBase; 106 mM Tris-HCl; 2% SDS; BPB; pH about 8.5; 50 mM DTT; 35% Glycerol).

The protein concentration of each sample was estimated by loading defined volumes of each sample to a one dimensional SDS-polyacrylamide gel electrophoresis (SDS-PAGE) gel (Criterion XT-precast gel: Biorad, Cat #345-0119, lot #CX070706B2), which contained a serial dilution of calibrated amounts of rat proteins from whole liver cell lysates and was electrophoresed in a BioRad Criterion electrophoresis device according to manufacturer's instruction. The gel was stained using Sypro Ruby according to manufacturer's instructions. Briefly, the gels were fixed 2×30 min in aqueous solution containing 50% methanol, 7% acetic acid, followed by staining overnight in Sypro Ruby solution (Molecular Probes, #S12001). Gels were washed for 30 min in 10% methanol, 7% acetic acid, and then for 2× 5 min in water. Protein staining with Sypro Ruby was quantified with a Diana III CCD-based digital imager (Raytest Isotopenmessgerate GmbH, Straubenhard Germany: Sypro Filter, 605 nm).

The intensity of protein staining of Sypro Ruby-stained gel lanes was compared between standard proteins and patient urine samples. For supernatants the whole lane was used for determination. For urine Pellet samples only the lane area below the dominating Uromodulin band was considered, resulting in a "uromodulin corrected protein concentration."

Annexin A3 and neutrophil gelatinase-associated lipocalin (NGAL, SWISSPROT Accession P80188, a marker for Neutrophils) levels in each sample were quantified by loading normalized protein amounts to SDS-PAGE gels as described above, whereby each gel contained three replicate lanes of 2 µg of a standardized protein extract from PC3 human prostate cancer cell line, which contained a convenient reference amount of both annexin A3 and NGAL. Proteins from these gels were western blotted onto PVDF (polyvinylidene fluoride) membranes according to standard methods for 1.5 h at 15V constant voltage and a limit of 3 mA/cm².

The non-specific protein binding sites on blotted membranes were blocked by 2 h incubation with gentle shaking in TBS (175 mM NaCl, 3.5 mM KCl, 20 mM Tris, pH 7.4) containing 5% redissolved dried milk powder. Primary antibodies were added specific for annexin A3 (1:20000 dilution, polyclonal rabbit anti-human Annexin A3) or NGAL (1:500 dilution, anti-human Lipocalin, polyclonal, from goat, R&D Systems, Nr. AF1757, lot JBH025051). After incubation at room temperature for 2 h the buffer was removed, washed three times for 10 min with TBS, and then incubated with the appropriate respective second antibodies against rabbit IgG (goat anti-rabbit-IgG pre-absorbed with human IgG and mouse IgG, couples to horse radish peroxidase: Santa Cruz, #sc-2054, lot #G2005. 1:5000 dilution) or goat IgG (Anti-goat IgG, from rabbit, pre-absorbed with human IgG and mouse IgG, coupled to horse radish peroxidise. Santa Cruz Biotechnology, #sc-2922 lot #C1405. 1:5000 dilution). Enhanced chemiluminescence (ECL) was measured afer addtion of Super Signal West Dura, Pierce (0.1 ml/cm²).

Values of NGAL or annexin A3 signals were normalized to the average signal from each of the three reference PC3 lanes on each gel, and the normalized annexin A3 or NGAL values were used for the statistical analysis. From these values, the levels of both proteins were calculated relative to the absolute sample volume, and also normalized to protein concentration. These values were calculated separately for pellet and supernatant, as well as for the ratio of pellet:supematant. Parameters that were correlated to cancer and compared to PSA values are summarized in Table 2.

Clinical parameters recorded included blood PSA levels, free total PSA levels, and complexed PSA levels, as well as histological evaluation of prostate tissue biopsies that were obtained following donation of exprimate urine, during the course of a standard digital rectal examination (DRE). In cases where high levels of serum PSA and DRE indicated necessity of prostectomy, the histological evaluation was performed on that material without prior biopsy.

The above data parameters were included in the statistical analysis, that included also clinical data recorded in the hospital. Prostate biopsies or prostectomy were obtained from all patients, and the clinician made a diagnosis of positive or negative for PCa based on histological examination of the tissue. Blood PSA levels were also obtained according to standard clinical practices. The U.S. Food and Drug Administration (FDA) has approved the PSA test for annual screening of prostate cancer in men of age 50 and older. PSA levels between 4 and 10 ng/mL (nanograms per milliliter) are considered to be suspicious and should be followed by rectal ultrasound imaging and, if indicated, biopsy. PSA is false positive- and false negative-prone. Biopsy-detected prostate cancer, including high-grade cancers, is not rare among men with PSA levels of 4.0 ng/mL or less—levels generally thought to be in the normal range.

Figure 8:
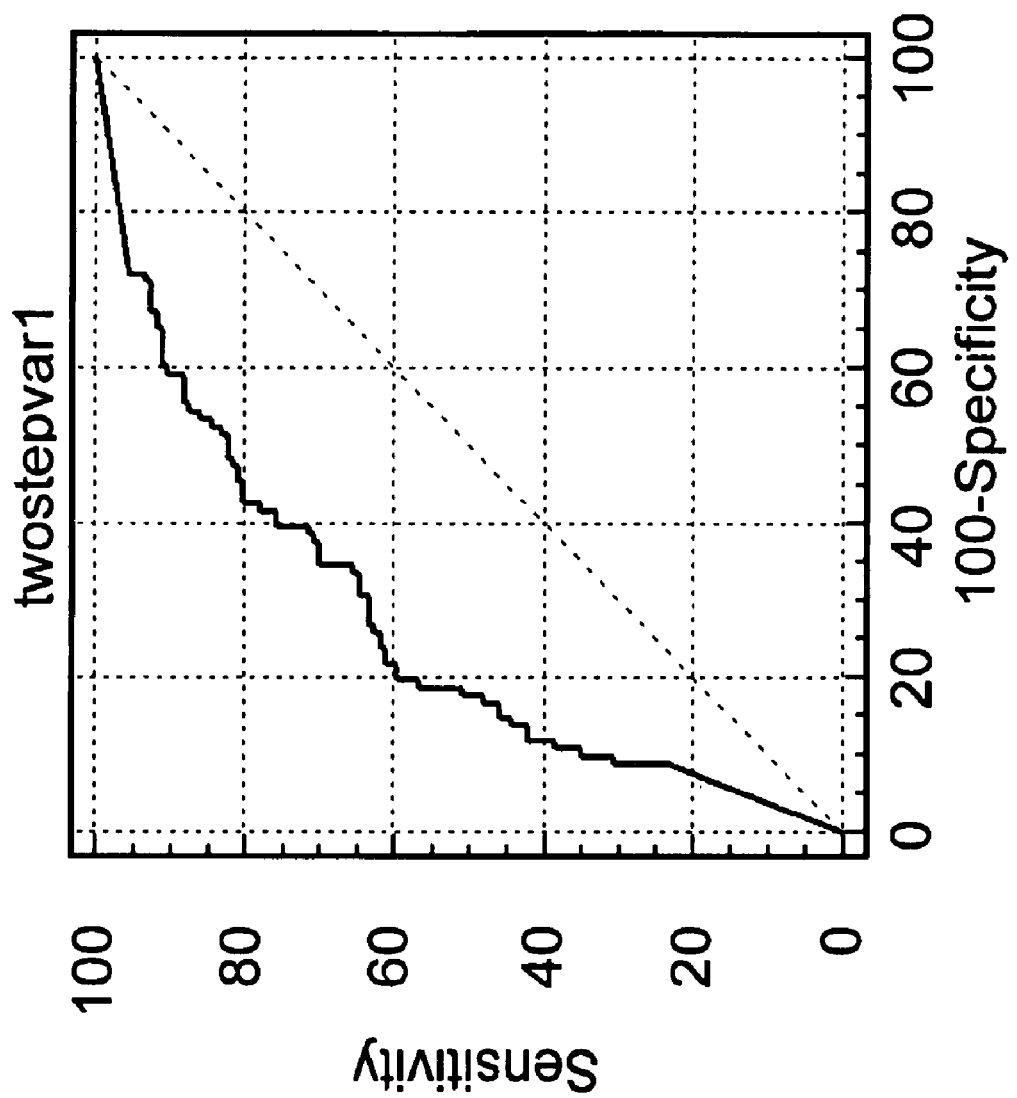
FIG. 8: ROC Curve—Two-Step Procedure 1:
"Use U_ANX_tot if $2.5 \leq PSA\_ini \leq 12$, most obvious decision otherwise"
Legend:
VARIABLE=IF(PSA_ini<2.5;100000; IF(PSA_ini<=12; u_anx_tot; 0)) twostepvar1
CLASSIFICATION VARIABLE: PCa
POSITIVE GROUP: PCa=1
Sample size=137
NEGATIVE GROUP: PCa=0
Sample size=101
Disease prevalence (%)=57.6
Area under the ROC curve=0.740
Standard error=0.033
95% Confidence interval=0.679 to 0.794
P (Area=0.5)<0.0001
Figure 9:
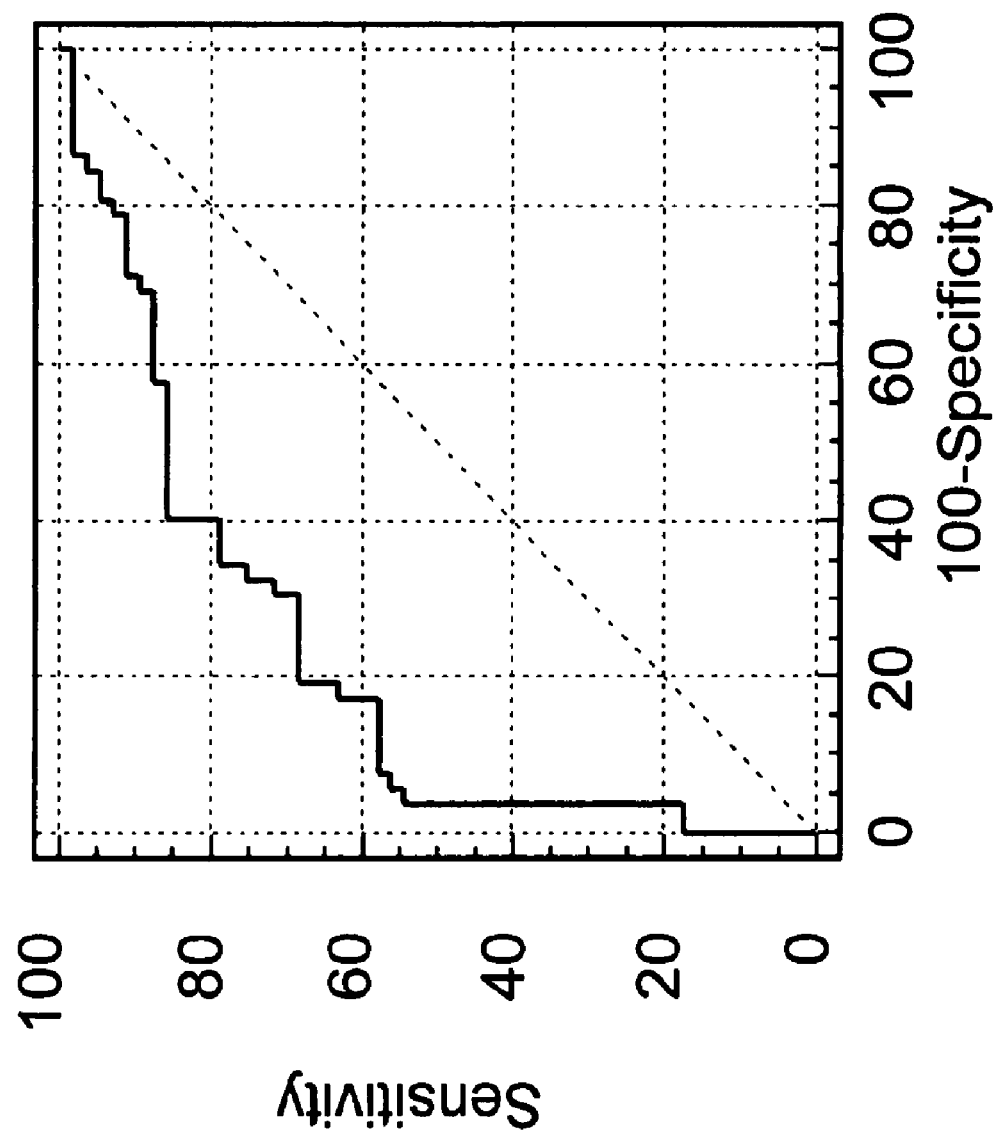
FIG. 9: ROC Curve—T comb.var.anx.psa2:
=−2.386+3.294 log(1+PSA_ini)−0.475 log(1+PU_ANX tot)
Legend:
select: AND(PSA_ini>=2;PSA_ini<=6)***
classification variable PCa
positive group: PCa=1, Sample size=57
negative group: PCa=0, Sample size=52
Disease prevalence (%)=52.3

The dataset consists of composite data files from 250 patients. Initial PSA values were available in 243 of the 250 patients and were missing for 7 patients. Furthermore, two of the latter seven patients and five other patients lacked the histological results of the biopsy (prostate cancer yes/no). Hence, all results presented here only use the data on those 243 patients whose PCa status is known: 140 patients with positive and 103 with negative PCa diagnosis. In FIGS. 8 and 9, the Receiver Operating Characteristic (ROC) curves generated using the clinical results are presented using inverse values for all ROC curves other than for PSA; i.e., the areas under the ROC curves were observed to correlate with higher PSA values in cancer patients, and with a lower average annexin A3 signal measured for cancer patients.

The area under the ROC curve (AUROC) for PSA was 0.684, which is significantly different from an AUROC of 0.5, but somewhat artificially high due to patient recruitment in participating clinics, (as known to every expert in the field). However we do note that our patient collective had an unusually high proportion of cancer patients (57%) because some of the patients had been examined by our test clinics after having providing high PSA readings at other centres. The AUROC values for the individual annexin A3-based variables measured are in the same range (the maximum is attained by PU_ANX_tot, AUROC 0.666; data not shown), and also significantly different from 0.5. Thus annexin A3 could also be used to replace PSA entirely, because in the crucial grey zone of PSA (2-6 ng/ml and 4-10 ng/ml), annexin 3 offers considerable advantages (see ROC curves 0.78 and 0.791 in Tables 4-6) with high specificities at acceptable sensitivities, and shows a similar overall performance, considering the whole range of PSA-values.

There was no preselection for annexin A3 in our patient selection, and there was no correlation between annexin A3 values and PSA values, indicating that annexin A3 expression/secretion and PSA entry to the bloodstream are regulated by separate mechanisms. We observed no correlation between either PSA or annexin A3 levels with patient age. Presumably the high proportion of cancer-positive patient, some of whom were preselected on the basis of suspiciously high PSA values measured at other centers, upset the expected higher abundance of PSA levels that would be expected with increasing age. However, as annexin A3 was not preselected it is concluded that its levels are probably not age-related.

Particular emphasis is placed on the statistical analysis of the subpopulation of patients with initial PSA values in the interval 2 ng/mL to 6 ng/mL. Again, all seven AUROC values for the measured individual parameters are significantly different from 0.5, although only 57 PCa patients and 52 non-PCa patients meet the PSA criterion defining the subpopulation. In contrast to the overall results, the AUROC of PSA_ini is no longer the largest one, but is superceded by five of the six AUROC values of annexin A3 based variables (P_ANX_ug being the only exception). The highest AUROC value, 0.735, is attained by PU_ANX_tot.

Besides the PSA range 2 ng/mL-6 ng/mL the PSA range 2.5 ng/mL-12 ng/mL is of special interest: In this subpopulation PSA_ini itself performs poorly (AUROC 0.580), while U_ANX_tot performs best (AUROC 0.693). Thus, this PSA range seems appropriate to assess the characteristics of the following two-step procedure, which is presented by way of methodical demonstration:

In the first step patients are assigned to one of three classes depending on their initial PSA value:

PSA_ini<2.5→low PCa risk,

PSA_ini>12→high PCa risk,

PSA_ini in [2.5, 12]→application of a test based on U_ANX_tot as a second step deciding whether or not invasive diagnostic procedures are indicated.

(The first two cases are referred to as the "most obvious decision" in the caption of FIG. 8.)

This two-step procedure is then incorporated into a single variable, here called twostepvar1, by defining $$\text{twostepvar1} := \begin{cases} 100000, & \text{if PSA\_ini} < 2.5 \\ \text{U\_ANX\_tot}, & \text{if PSA\_ini} \in [2.5, 12] \\ 0, & \text{if PSA\_ini} > 12. \end{cases}$$

Low values of U_ANX_tot indicate an increased risk of prostate cancer and high values a lower risk. The value 100000 is chosen in order to ensure that it should always be greater than the largest U_ANX_tot value actually measured. The performance of twostepvar1 can be seen in FIG. 8. (The constancy of twostepvar1 for PSA_ini values below 2.5 and beyond 12 causes the ROC curve to start and end with a noticeable straight line segment.) The AUROC of 0.740 is of course highly significantly different from 0.5. Moreover, a comparison with the conventional PSA test is enlightening: For example, the criterion "PSA_ini>4" leads—in this analysis data set—to a sensitivity of 80.3% and a specificity of 49.5%. The same sensitivity, 80.3%, is gained by using the criterion "twostepvar1<450", but now a specificity of 57.4% is achieved.

The example of FIG. 8 demonstrates the principles of stepped AUROC values which rely on different meausurements (PSA or annexin A3 values) depending upon the PSA level. These principles, as will be obvious to experts, are the same as used in several results presented in Tables 4-6, and which provide higher AUROC values. The excellent performance of cancer prediction of the annexin A3 variables in patients with intermediate levels of serum PSA is further evidenced by considering the annexin A3-based multiple variables for patients with intermediate PSA values.

According to the methods and strategies demonstrated above, ROC curve analysis was performed for the parameters shown in Tables 3-6. Additionally to those variables, ROC curve analysis was performed using the following parameters generated by logical regression analysis:

anx.comb.var is based upon logical regression analysis using the combined U_ANX_ug und U_ANX_tot as variables according to the following relationship.

$=4.463+2.906 \log(1+U\_ANX\_ug)-0.790 \log(1+U\_ANX\_tot)$ comb.var.anx.psa1 is based upon logical regression analysis using the combined PSA_ini und U_ANX_tot as variables according to the following relationship.

$=0.254+1.046 \log(1+PSA\_ini)-0.342 \log(1+PU\_ANX\_tot)$ comb.var.anx.psa2 is based upon logical regression analysis using the combined PSA_ini und PU_ANX_tot as variables according to the following relationship.

$=-2.386+3.294 \log(1+PSA\_{ini})-0.475 \log(1+PU\_ANX\_tot)$.

While extremely high or extremely low PSA values provide relatively reliable assignment of cancer/non-cancer status, the results of Tables 4-6 clearly demonstrate that various combinations of annexin A3-based parameters outperform PSA for intermediate values of PSA. Thus, the measurement of annexin A3 levels in exprimate urine supernatants or pellets, preferably including supernatant to pellet ratios, provides improved diagnostic reliability.

To demonstrate the utility of these results, the ROC curve for comb.var.anx.psa2 is presented in detail in FIG. 9, and Table 7. This ROC curve is based only on patients with PSA values between 2 ng/mL and 6 ng/mL, and gives a highly significant AUROC value of 0.791 despite the use of only 109 patients in this range for the analysis. Furthermore, this ROC curve exhibits an extremely steep climb in sensitivity (true positive fraction) relative to specificity (true negative fraction), which is quite advantageous regarding predictive value. For instance at a sensitivity level of 54% the specificity is 96% (FIG. 9, Table 7). The ROC curve for anx.comb.var performed similarly, with sensitivity of 38% having specificity of 91% (AUROC 0.78) for the PSA range 4 ng/mL to 10 ng/mL. The data disclosed here demonstrate convincingly that annexin A3 is a novel and powerful marker for prostate cancer, that is especially powerful in those patients where PSA values are the least reliable.

Taken together, the third comprehensive study which was double-blinded and multi-center, showed, that the most robust and statistically significant diagnostic read-out was the annexin A3-amount in supernatants of exprimate urines after prostatic massage which have been obtained during a standard clinical procedure (DRE) due for potential prostate cancer patients with a standard low speed centrifugation. This is very favorable because it allows direct access to ELISA-based or other antibody-based assays without prior solubilization of pelleted samples (danger of interference by detergents, salts, chemicals etc.). This annexin A3-amount in supernatants is inversely correlated with cancer, in non-cancers, annexin A3-amounts are higher, with certain indications that additional and sequential profiling of non-cancer cases can even improve the overall diagnostic value.

The results are completely in line with the first two studies, which were smaller and in some aspects incomplete concerning sample collection and sample control. The first study only included pellets (FIG. 6), yet nevertheless here it was found the inverse correlation for cancer patients. In this study a group of healthy volunteers were included, which was not the case for subsequent studies. During the second study which did take into account supernatant-annexin A3 and pellet-annexin A3 (albeit with sample numbers which were too small to come to statistically significant solutions), there was a trend to higher supernatant to pellet ratios in cancer patients as compared to BPH and other non-cancers. This is perfectly in line with the first and third study, because obviously the low pellet annexin A3-amounts combine in cancer patients with a slightly higher annexin A3-amount to bigger ratios (FIG. 7). In non-cancers (like, e.g., BPH, fibrosis and others), obviously in total the considerably larger annexin A3-amounts in pellets and supernatants combine to lower overall ratios. The robustness of the annexin A3-signal in supernatants provides an experimental and clinical advantageous and easy diagnostic read-out.

REFERENCES

1. Carter, H. B. et al., "Improved Biomarkers for Prostate Cancer: A Definite Need," *Journal of the National Cancer Institute*, Jun. 2, 2004, vol. 96, no. 11, pages 813-815.
2. Antenor, J.A. et al., "Relationship between Initial Prostate Specific Antigen Level and Subsequent Prostate Cancer Detection in a Longitudinal Screening Study," *The Journal of Urology*, Jul. 2004, vol. 172, pages 90-93.
3. Lilja, H., "Biology of Prostate-Specific Antigen," *Urology* 62 (Supplement 5A), November 2003, pages 27-33.
4. Watson, R. W. et al., "Future Opportunities for the Diagnosis and Treatment of Prostate Cancer," *Prostate Cancer Prosiatic Diseases*, 2004, vol. 7, pages S8-S 13.
5. Demarzo, A. M. et al., "Pathological and Molecular Aspects of Prostate Cancer," *The Lancet*, Mar. 15, 2003, vol. 361, pages 955-964.
6. Kumar-Sinha, C. et al. "Molecular Markers to Identify Patients at Risk for Recurrence after Primary Treatment for Prostate Cancer," *Urology* 62 (Supplement 6B), Dec. 29, 2003, pages 19-35.
7 Moul, J. W. et al., "Molecular Markers in Prostate Cancer: The Role in Preoperative Staging," *Clinical Prostate Cancer*, June 2002, pages 42-50.
8. Ahram, M. et at., "Proteornic Analysis of Human Prostate Cancer," *Molecular Carcinogenesis*, 2002, vol. 33, pages 9-15.
9. Petricoin, E. F. et at., "Proteomic Approaches in Cancer Risk and Response Assessment," *Trends Molecular Medicine*, February 2004, vol. 10, no. 2, pages 59-64.
10. Diamandis, E. P., "Mass Spectrometry as a Diagnostic and a Cancer Biomarker Discovery Tool: Opportunities and Potential Limitations," *Molecular & Cellular Proteomics*, 2004, vol. 3, pages 367-378.
11. Jacobs, I. J. et al., "Progress and Challenges in Screening for Early Detection of Ovarian Cancer," *Molecular & cellular Proteomics*, 2004, vol. 3, pages 355-366.
12. Lapointe, J. et al., "Gene Expression Profiling Identifies Clinically Relevant Subtypes of Prostate Cancer," *PNAS*, Jan. 20, 2004, vol. 101, no. 3, pages 811-816.
13. Rossi, S. et al., "Fatty Acid Synthase Expression Defines Distinct Molecular Signatures in Prostate Cancer," *Molecular Cancer Research*, August 2003, vol. 1, pages 707-715.
14. Pames, H. L. et al., "Prostate Cancer Chemoprevention Agent Development: The National Cancer Institute, Division of Cancer Prevention Portfolio," *The Journal of Urolopy*, February 2004, vol. 171, pages S68-S75.
15. Eastham, J. A., "Multimodal Treatment Strategies Combining Neoadjuvant Hormonal Therapy and/or Chemotherapy with Radical Prostatectomy in High-Risk Localised Prostate Cancer," *Expert Opinion Investigating Drugs*, 2004, vol. 13, pages 39-46.
16. Nebert, D.W. et al., "Pharmacogenomics and 'Individualized Drug Therapy': High Expectations and Disappointing Achievements," *Am. J. Pharmacogenomics*, 2003, vol. 3, pages 361-370.

17. Gerke, V. et al., "Annexins: From Structure to Function," *Physiol. Rev.*, April 2002, vol. 82, pages 331-371.
18. Alaiya, A. A. et al., "Identification of Proteins in Human Prostate Tumor Material by Two-Dimensional Gel Electrophoresis and Mass Spectrometry," *CMLS Cellular and Molecular Life Sciences*, 2001, vol. 58, pages 307-311.
19. Niimi, S. et al., "Expression of Annexin A3 in Primary Cultured Parenchymal Rat Hepatocytes and Inhibition of DNA Synthesis by Suppression of Annexin A3 Expression Using RNA Interference, " *Biol. Pharm. Bull.*, 2005, vol. 28, no. 3, pages 424-428.
20. Niimi, S. et al., "Specific Expression of Annexin III in Rat-Small-Hepatocytes," *Biochemical and Biophysical Research Communications*, 2003, vol. 300, pages 770-774.
21. Schartz, N. E. et al., "From the Antigen-Presenting Cell to the Antigen-Presenting Vesicle: The Exosomes," *Current Opinion in Molecular Therapeutics*, 2002, vol. 4, no. 4, pages 372-381.
22. Pisitkun, T. et al., "Identification and Protcomic Profiling of Exosomes in Human Urine," *PNAS*, Sep. 7, 2004, vol. 101, no. 36, pages 13368-13373.
23. Thery, C. et al., "Proteomic Analysis of Dendritic Cell-Derived Exosomes: A Secreted Subcellular Compartment Distinct from Apoptotic Vesicles," *Journal of Immunology*, 2001, vol. 166, pages 7309-7318.
24. Carlsson, L. et al., "Dominant Prostasome Immunogens for Sperm-Agglutinating Autoantibodies of Inifertile Men," *Journal of Andrology*, September/October 2004, vol. 25, no. 5, pages 699-705.
25. Oh, P. et al., "Subtractive Proteomic Mapping of the Endothelial Surface in Lung and Solid Tumours for Tissue-Specific Therapy," *Nature*, Jun. 10, 2004, vol. 429, pages 629-635.
26. Reutelingsperger, C. P. et al., "Annexin V, the Regulator of Phosphatidylserine-Catalyzed Inflammation and Coagulation during Apoptosis," *CMLS Cellular and Molecular Life Science*, 1997, vol. 53, pages 527-532.
27. Perretti, M. et al., "Annexin 1 and the Biology of the Neutrophil," *Journal of Leukocyte Biology*, July 2004, vol. 75, pages 25-29.
28. Maderna, P. et al., "Modulation of Phagocytosis of Apoptotic Neutrophils by Supernatant from Dexamethasone-Treated Macrophages and Annexin-Derived Peptide Ac(2-26)," *The Journal of Immunology*, 2005, vol. 174, pages 3727-3733.
29. Hegmans, J. P. et al., "Proteomic Analysis of Exosomes Secreted by Human Mesothelioma Cells," *American Journal of Pathology*, May 2004, vol. 164, no. 5, pages 1807-1815.
30. Wang, W. et al., "Annexin-Mediated Ca2+ Influx Regulates Growth Plate Chondrocyrte Maturation and Apoptosis," *The Journal of Biological Chemistry*, Feb. 7, 2003, vol. 278, no. 6, pages 3762-3769.
31. Bondanza, A. et al., "Inhibition of Phosphatidylserine Recognition Heightens the Immunogenicity of Irradiated Lymphoma Cells In Vivo," *J. Exp. Med.*, Nov. 1, 2004, vol. 200, no. 9, pages 1157-1165.
32. Kamal, A. M. et al., "An Annexin 1 (ANXA 1)-Derived Peptide Inhibits Prototype Antigen-Driven Human T Cell Th1 and Th2 Responses In Vitro," *Clinical and Experimental Allergy*, 2001, vol. 31, pages 1116-1125.

The invention claimed is:

1. A method of diagnosing prostate cancer and discriminating between cancerous and non-cancerous prostate tissue, comprising the steps of:
   a) providing a prostate massage to a human;
   b) obtaining an exprimate urine sample from the human;
   c) fractionating the exprimate urine sample to produce an insoluble fraction and a supernatant fraction;
   d) determining the abundance of human annexin A3 protein in the insoluble fraction and/or supernatant fraction;
   e) providing a first control value for the abundance of human annexin A3 protein in an insoluble fraction and/or supernatant fraction from a second human known not to have prostate cancer, wherein the insoluble fraction and/or supernatant fraction is obtained from the second human by performing steps a)-d);
   f) comparing the abundance of human annexin A3 protein in the insoluble fraction and/or supernatant fraction to the first control value; and
   g) diagnosing the human as having prostate cancer and discriminating between cancerous and non-cancerous tissue, if the abundance of human annexin A3 protein in the insoluble fraction and/or supernatant fraction is less than the first control value; wherein the exprimate urine sample, or a fraction thereof, is purified and is free from neutrophils, monocytes or peripheral blood mononuclear cells.

2. The method according to claim 1, wherein the abundance of at least one further human protein is determined and wherein the at least one further human protein is selected from the group consisting of serum amyloid P, isopeptidase T, muscle-type fatty acid binding protein, galectin 1, heat shock protein 90, P11021-78 kDa glucose-regulated protein precursor, protein disulfide isomerase, epidermal-type fatty acid binding protein, enoyl coenzyme A hydratase, nucleophosmin, prosome, activator subunit 2,cytokeratin, KNP-1 alpha protein, KNP-1 beta protein, prostate specific antigen and prostate specific membrane antigen.

3. The method according to claim 1, further comprising determining the abundance in blood or serum of prostate specific antigen (PSA).

4. The method according to claim 1, wherein the insoluble fraction is used for determining the intracellular abundance of said human annexin A3 protein.

5. The method according to claim 1, wherein the supernatant fraction is used for determining the extracellular abundance of said human annexin A3 protein.

6. The method according to claim 1, wherein the abundance of human annexin A3 protein is determined by immuno-histochemical methods.

7. The method according to claim 1, wherein the exprimate urine sample, or fractions thereof, are from morning urine.

8. The method according to claim 1, further comprising measuring human annexin A3 levels in faeces or epithelial cells of the intestinal tract.

* * * * *